US007341998B2

(12) United States Patent
Gilly et al.

(10) Patent No.: US 7,341,998 B2
(45) Date of Patent: Mar. 11, 2008

(54) ***CONUS CALIFORNICUS* NEUROTOXINS**

(75) Inventors: William F. Gilly, Pacific Grove, CA (US); Zora Neofitovic-Lebaric, Carmel, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 11/382,679

(22) Filed: May 10, 2006

(65) Prior Publication Data

US 2006/0264374 A1 Nov. 23, 2006

Related U.S. Application Data

(60) Provisional application No. 60/679,876, filed on May 10, 2005.

(51) Int. Cl.
*A61K 38/17* (2006.01)
*C07K 14/435* (2006.01)
*A01N 63/00* (2006.01)

(52) U.S. Cl. ......................... 514/12; 530/324; 424/405

(58) Field of Classification Search .................. 514/12; 530/324; 424/405

See application file for complete search history.

(56) References Cited

OTHER PUBLICATIONS

Whysner et al., "Purification of the lethal fraction of the venom of the marine snail *Conus californicus*," Toxicon 4(3):177-181, 1966.*

Craig, A.G., et al., "An O-glycosylated neuroexcitatory *Conus* Peptide," (1998) *Biochemistry,* 37(46):16019-16025.

Duda, T.F., et al., "Evolutionary diversification of multigene families: allelic selection of toxins in predatory cone snails," (2000) *Mol. Biol. Evol.,* 17(9):1286-1293.

Duda, T.F., et al., "Gene expression and feeding ecology: evolution of piscivory in the venomous gastropod genus *Conus*," (2004) *Proc. R. Soc. Lond.,* 271:1165-1174.

Gilly, W.F., et al., "All-or-none contraction and sodium channels in a subset of circular muscle fibers of squid mantle," (1996) *Biol. Bull.* 191:337-340.

Gilly, W.F., et al., "Control of the spatial distribution of sodium channels in giant fiber lobe neurons of the squid," (1990) *Neuron,* 5:663-674.

Gilly, W.F., et al., "Fast and slow activation kinetics of voltage-gated sodium channels in molluscan neurons," (1997) *J. Neurophysiol.,* 77:2373-2384.

Gilly, W.F., et al., "Properties of appropriately and inappropriately expressed sodium channels in squid giant axon and its somata," (1989) *The Journal of Neuroscience,* 9(4):1362-1374.

Jones, R.M., et al., "Conotoxins—new vistas for peptide therapeutics," (2000) *Current Pharmaceutical Design,* 6:1249-1285.

Mathes, C., et al., "Fast inactivation of delayed rectifier K conductance in squid giant axon and its cell bodies," (1997) *J. Gen. Physiol.,* 109:435-448.

McFarlane, M.B., et al., "Spatial localization of calcium channels in giant fiber lobe neurons of the squid (*Loligo opalescens*)," (1996) *PNAS,* 93:5067-5071.

(Continued)

*Primary Examiner*—Rebecca S. Prouty
*Assistant Examiner*—Rosanne Kosson
(74) *Attorney, Agent, or Firm*—Bozicevic, Field & Francais LLP; Pamela J. Sherwood

(57) ABSTRACT

Novel conotoxin polypeptide and polynucleotide sequences are provided.

5 Claims, 7 Drawing Sheets

OTHER PUBLICATIONS

Schultz, J.R., et al., "The projectile tooth of a fish-hunting cone snail: *Conus catus* injects venom into fish prey using a high-speed ballistic mechanism," (2004) *Biol. Bull.*, 207:77-79.

Wang, C-Z., et al., "*Conus* peptides—a rich pharmaceutical treasure," (2004) *Acta Biochimica et Biophysica Sinica*, 36(11):713-723.

Bingham, J., et al., "A new highly selective conotixin from *Conus californicus* that targets voltage-gated neuronal Na* channels of squid," (2000) *The Journal of General Physiology*, 116:12a-13a.

Hansson, K., et al., "Isolation and characterization of three novel Gla-containing *Conus marmoreus* venom peptides, one with a novel cysteine pattern," (2004) *Biochemical and Biophysical Research Communications*, 319:1081-1087.

Terlau, H., et al., "*Conus* venoms: a rich source of novel ion channel-targeted peptides," *Physiology Review*, 84:41-68, 2004.

Whysner et al., "Purification of the Lethal Fraction of the Venom of the Marine Snail *Conus californicus*," Toxicon, 1966, vol. 4, pp. 177-181.

"International Search Report", International Searching Authority, May 7, 2007, PCT/US06/18132, 5 pages.

\* cited by examiner

Comparison of calTx1.1A cDNA sequence and N-terminal Edman peptide sequence

Mature toxin coding region calTx1.1 F1   calTx1.1 F2         calTx1.1 F3                                    calTx1.1 rev.
MKLTCVLVVLLLLPYGDLITNNYIRGAARKVTPWRRNLKTRDVCDSLVGGHCIHNGCWCDQEAPHGNCCDTDGCTAAWWCPGTKWD
                                 1                       20                               45

Edman sequence:
                                 DVCDSLVGGHCIHNGC_CDQ_A_HGNCCDTDG...

Figure 1

Based on the arrangement of cytokine residues, *caTx1.1A* represents a new class of *Conus* toxins related to an established family of *Conus* peptides that affect voltage-gated ion channels. Positions of Cys residues are indicated with the number of intervening amino acids. No sequence homology exists between these amino acids between the different toxin classes.

| toxin class | target channel type | | | | | | | | |
|---|---|---|---|---|---|---|---|---|---|
| *caTx1.1A* | | 2—C—7—C—4—C—1—C—8—C—4—CC—4—C—6 | | | | | | | |
| μO (2) | $Na_v$ | 1—C—6—C—9—CC—4—C—4—C—1 | | | | | | | |
| δ (5) | $Na_v$ | 1-3—C—6—C—6—CC—3-4—C—3-4—C—1-4 | | | | | | | |
| κ (1) | $K_v1$ | 0—C—6—C—6—CC—3—C—5—C—1 | | | | | | | |
| ω (8) | $Ca_v$ | 0-3—C—6—C—6-9—CC—2-3—C—3-6—C—0-3 | | | | | | | |

← novel N-terminal region →

Figure 4 calTx1.1 family of toxins based on cDNA sequences. CalTx1.1A-U are shown; they have been regrouped by eye into different groups. The original Edman sequence is given in the top row. The # seq column (rightmost) indicates the number of clones identified from PCR amplifications from 16 individual snails. No entry means that sequence was not identified in an individual snail, only in pooled material.

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | # seq |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Edman seq | D | V | C | D | S | L | V | G | G | H | C | I | H | N | G | C | X | C | D | Q | X | A | X | H | G | N | C | C | D | T | D | G | T | A | A | W | W | C | P | G | T | K | W | D | | |
| 1.1A=calTx1.1 | D | V | C | D | S | L | V | G | G | H | C | I | H | N | G | C | W | C | D | Q | E | A | P | H | G | N | C | C | D | T | D | G | T | A | A | W | W | C | P | G | T | K | W | D | | 36 |
| 1.1B =5-10 | | | | | | | | | | | | | | | | | | | | | | | | | | | | | | | | | | | R | | | | | | | | F | | | 21 |
| 1.1C =5-20 | | | | | | | E | | | | | | | | | | | | | E | | | | | | | | | | | | | | | W | | | | | | | | | | | 8 |
| 1.1D =12-01 | | | | | | | E | | | R | | | | | | | | | | E | R | | D | | | | | | | | | | | | W | | | | | | | | F | | | 2 |
| 1.1Q =96-26 | | | | | | | E | | | R | | | | | | | | | | E | R | | D | | | | | | | | S | | | | W | | | | | | | | | | | 56 |
| 1.1E =Q7 | | | | | | | | D | | R | | | | | | | | | | E | R | | D | | | | | | | | A | | | | R | | | | | | | | | | | 1 |
| 1.1F =Q5 | | | | | | | | D | | R | | | Y | | | | Y | | | E | R | | D | | | | | | | | A | | | | R | | | | | | | | | | | 33 |
| 1.1G =35-36 | | | | | | | | D | | R | | | | | | | | | | E | R | | D | | | | | | | | A | | | | R | | | | | | | | | | | |
| 1.1U =96-23 | | | | | | | | D | | R | | | | | | | | | | E | R | | S | | | | | | | | | | | | R | | | | | | | | | | | |
| 1.1I =Q14 | | | | | | | | | | R | | | | | | | | | | E | R | | S | | | N | | | | | S | | | V | R | | | | | | | | | | | 8 |
| 1.1K =Q11 | | | | | | | | | | R | | | | | | | | | | E | R | | S | N | | E | | | | | S | | | | | | | | | | | | | | | 1 |
| 1.1L =Q17 | | | | | | | | | | R | | | F | | | | F | | | E | R | | S | N | | N | | | | | S | | | | R | T | | | | | | | L | F | | 1 |
| 1.1J =Q1 | | | | | | | | | | R | | | | | | | | | | E | R | | S | | | | | | | | S | | | | R | T | F | | | | | | | F | | |
| 1.1R =85-23 | | | | | | | | | | R | | | F | | | | F | | | E | R | | S | | | | | | | | G | | | | T | T | F | | | | | | | F | | |
| 1.1S =85-17 | E | S | V | A | | | | | | R | | | F | | | | F | | | E | R | | S | | | | | | | | S | | | V | W | W | | | | | | | | | | |
| 1.1T =85-31 | | | | | | | | | | R | | | | | | | | | | E | R | | S | N | | | | | | | G | | V | | R | | | | | | | | | | | 1 |
| 1.1H =Q2 | | | | | | | | E | | R | | | | | | | | | | E | S | | S | N | | | | | | | G | | V | | W | | | | | | | | | | | 414 |
| 1.1M =12-16 | | | | | | | | D | | R | | | | | | | | | | E | S | | S | N | | | | | | | G | | V | | W | | | | | | | | | | | |
| 1.1N =Q3 | K | K | | S | P | | | | | R | | | | | | | | | | E | S | | K | | | | | | | | G | | | | W | | | | | | | | | | | |
| 1.1O =5-32 | | | | | | | | | | R | | | | | | | | | | E | S | | K | | | | | | | | | | | | | | | | | | | | | | | |
| 1.1P =5-31 | | | | | | | K | | | K | | | | | | | | | | E | D | | K | | | | | | | S | G | | S | G | V | K | | | | | | | | G | | 1 |

Original Edman sequence could not be unambiguously assigned beyond Q20 (except for H24) without aid from cDNA sequence. Given the predominance of A and B in cDNAs found, a mixture of A and B is possible.

Comparison of calTx1.1A putative peptide sequence with sequences deduced for the calTx1.2 family.

*prohormone* → *toxin coding region* calTx1.1A

R K Y T P V R R N L K T R D Y C D S L V G G H C I H N G C W C D D Q E A P H G N C C D D T D G C T A A V V C P G T K W D calTx1.2 family

| R G A T P V Q N S L K A R G V C S T P E G S C V H N G C I C C H Q N A P C C H P S G C N W A N V C P G F L W D K N |

(with variants: R, R, R, R, R, R prefix column; substitutions M, H, A, Y shown in specific positions)

Figure 5

Most classes of toxins in *Conus californicus* have multiple isoforms

4 C sequences
*ca*/Tx3.1 (1)
Wp23 (7)
Wp33 (4)
Cl86 (3)
Wp9 (4)
Wp1 (4)
Cl37 (1)
Wp0 (1)
Cl163 (1)

9 classes, 26 peptides

6 C sequences
*ca*/Tx2.3 series (7)
*ca*/Tx2.1 (1)
*ca*/Tx2.2 (1)
*ca*/Tx2.4 (1)
Wp54 (5)
Wp66 (3)
Cl81 (1)

7 families, 19 peptides

8 C sequences
*ca*/Tx1.1 series (20)
*ca*/Tx1.2 series (7)
Wp31 (5)

3 families, 32 peptides

Total: 19 novel families, 77 peptide isoforms to date

FIGURE 6

| Leader | Pro-region |
| --- | --- |
| MKLTCVLVVLLLLLPYGDLI | TNNYIRGAAARKVTPWRRNLKTR | calTx1.1F1 → CTX2F →    Albert CTXF4 →

Toxin coding region

DVCDSLVGGHCIHNNGCWCDQEAPHGNCCDTDGCTAAWWCPGTKWD--ccpisagcavlsapsyamrcvpl

5' UTR
ccpisagcavlsapsyamrcvpl

CTXF5 →    ← calTx1.1rev    ← CTX2R

FIGURE 7

CONUS CALIFORNICUS NEUROTOXINS

This application claims priority to Provisional Application No. 60/679,876, filed on May 10, 2005.

This invention was made with Government support under contract IBN-0131788 awarded by the National Science Foundation. The Government has certain rights in this invention.

The genus of predatory cone snails (*Conus*) comprise more than 500 species. These species inhabit reef environments throughout the world. According to their prey preference, cone snails are generally classified into three major groups: the piscivorous preying upon fish, the molluscivorous eating mollusk, and the vermivorous feeding upon polychaete annelids. An outlier to this classification system is *Conus californicus*, which preys on all three groups. All cone snails are venomous predators. Owing to the highly toxic peptides stored in their venoms, these predators can easily immobilize and capture more agile preys, as well as escape from and defend against their predators and possibly deter competitors.

*Conus* species have developed many distinct venoms as a survival strategy for feeding and defense. Their venoms contain a diverse mixture of biologically active peptides, mostly small and structurally constrained. *Conus* peptides have been optimized to target specific ion channels, cell-surface receptors and transporters with very high affinities and selectivities. Various classifications and groupings have been made, usually on the basis of the arrangement of cysteine residues. *Conus* peptides discovered up to now have been clustered into eleven superfamilies, which have biological activities including: competitive and non-competitive acetylcholine receptor antagonist; 1 adrenoceptor antagonist; voltage-gated potassium channel blocker; voltage-gated sodium channel blocker; Pacemaker-channel blocker; voltage-gated calcium channel blocker; $5-HT_3$ receptor antagonist; presynaptic $Ca^{2+}$ channel blocker; noradrenaline transporter inhibitor; vasopressin receptor agonist; NMDA receptor antagonist; neurotessin receptor agonist; and the like. Conotoxins targeting ion channels have been most widely studied. Many kinds of ion channels are targeted by conotoxins, such as potassium, calcium and sodium channels. Conotoxins can modulate ion channels in various modes, such as block, potentiation or inactivation. Even in a single *Conus* species there are several distinct polypeptides with similar biological function but selectively aiming at a different subtype of a common target. The structure-function relationships of these proteins are reviewed by Jones et al (2000) Curr. Pharm. Des. 6:1249-1285.

Each *Conus* peptide is encoded by a single mRNA and processed from a precursor, usually between 70 and 120 amino acids in length. The prepro-peptide precursor has a distinct structural arrangement a highly conserved signal sequence at the N-terminus (the 'pre-region'), a conserved intervening spacer (the 'pro-region') and the hypervariable mature peptide at the C-terminus. Although the mature sequences from different or even the same species can vary greatly with each other, the signal sequences of *Conus* peptides within all members of a same superfamily are extremely conservative, and their pro-regions relatively conserved Peptide diversification apparently arises by focal hypermutation of the C-terminal toxin-encoding region. Several hypotheses (such as gene recombination, conversion and replication) have been suggested for the molecular basis of focal hypermutation. The mature toxin region may adopt many forms of non-synonymous and synonymous replacements, deletions and additions for its hypermutation. All these mutations are restricted within the intercysteine loops, whereas the rigid disulfide structural frameworks of the peptides remain unchanged.

The post-translational modifications of *Conus* peptides are significant. For example, contulakin-G has a disaccharide attached to its Thr residue at position 10, which significantly enhances its poency. Although little is known about the molecular mechanisms of most of these post-translational modifications, sequence elements within conopeptide precursors and specialized *Conus* cellular components involved in these processes have been clearly identified. Modifications include hydroxylation of proline; amidation of C-terminus; carboxylation of glutamic acid; bromination of tryptophan; isomerization of tryptophan from L- to D-form; cyclization of N-terminal Gln; sulfation of tyrosine; and O-Glycosylation.

*Conus* peptides comprise diverse classes of pharmacologically active small peptides. Each *Conus* species has its own distinct repertoire of venom peptides, and the venom peptides from different species are surprisingly divergent in sequence. It is estimated that more than 50,000 unique peptide sequences will be found in the genus. Each of these components is believed to have its specific biological target, including: ion channels, cell-surface receptors and neurotransmitter transporters. Such high target specificity and affinity of *Conus* peptides offers targeting and drug development for the treatment of many disorders, including neuropathic pain, cancer pain, epilepsy, muscle relaxants, e.g. for use in combination with anesthetic, and the like.

SUMMARY OF THE INVENTION

Conotoxin nucleic acid compositions and their encoded polypeptides and variants thereof are provided. Conotoxins are novel polypeptides that have potent pharmacologic activity, particularly in the blocking of voltage gated and chemically gated ion channels, e.g. voltage gated sodium channels. The polypeptides find use as therapeutic and research agents. The nucleic acid compositions find use in identifying homologous or related genes; for production of the encoded peptide; in producing compositions that modulate the expression or function of its encoded protein; for therapy; mapping functional regions of the protein; and in studying associated physiological pathways.

BRIEF DESCRIPTION OF THE DRAWINGS

FIG. 1 compares the partial sequence of calTx1.1A SEQ ID NO:101, determined from the purified peptide, with the complete gene sequence deduced from the corresponding cDNA SEQ ID NO:1.

FIG. 2 aligns the cysteine frameworks for families of previously described conotoxins that target voltage-gated ion channels from other species with the newly discovered class of calTx1.1 toxins.

FIG. 3 illustrates the effect of calTx1.1 in blocking neuronal voltage-gated Na channels.

FIG. 4 shows the diversity of predicted toxin sequences for the calTx1.1 family from *C. californicus* venom (isoforms calTx1.1A-U) based on Edman sequence, SEQ ID NO:101 and the deduced TX1.1 sequence. SEQ ID NO:1.

FIG. 5 compares the full-length calTx1.1A toxin-coding region SEQ ID NO:1 and part of the prohormone region with corresponding sequences deduced for the calTx1.2 family SEQ ID NO:22, residues 29-84.

FIG. 6 is a block diagram illustrating the different classes of *C. californicus* toxins and numbers of identified members and isoforms.

FIG. 7 is a summary of identification of calTx1.1 isoforms SEQ ID NO:6, residues 1-42 and SEQ ID NO:102 (and others).

DETAILED DESCRIPTION OF THE EMBODIMENTS

The invention provides a library of polypeptides derived from RNA isolated from the venom ducts of *Conus californicus*. Peptide toxins from the venoms of marine snails of the genus *Conus* are widely recognized to have application to a broad range of human disorders. *Conus californicus* possesses a large library of putative peptide toxins and agents that are significantly different from those of all other known *Conus* species. This species has not been previously studied at the molecular level in order to identify sequences for specific peptides.

The toxins of *C. californicus* have evolved independently of the rest of the genus. The cysteine-frameworks of the peptides, which are taken to define different "conventional" *Conus* peptides, are generally not in congruence with those of all other known *Conus* species. There is essentially no sequence homology of toxin-encoding genes between *C. californicus* and other *Conus* species at the amino acid or nucleotide level, and all published molecular phylogeny studies have indicated that *C. californicus* is only distantly related to other *Conus* species. These findings demonstrate that *C. californicus* toxins are all significantly different than those of other *Conus* species. The toxins are therefore likely to interact with different binding sites on target receptors in other organisms, and the array of organisms targeted will be different than those of tropical *Conus* species.

Although it has been established for some time that *C. californicus* is unusually omnivorous and that it is genetically distant from all other *Conus* species, only recently has work in the applicants laboratory shown unexpectedly that *C. californicus* can kill and consume live fish prey. This is significant, because toxins that affect fish therefore affect vertebrates. The diversity and nature of complexity in the putative peptide toxins was completely unexpected, and several features of this diversity and complexity are unique to *C. californicus*.

The peptide library information from *C. californicus* adds a significant dimension to the field of peptide pharmaceuticals and basic research tools. Much work at present is being expended on the toxins of other *Conus* species.

Peptides described herein clearly have application in a wide variety of human and animal disorders of the nervous system, cardiovascular system, muscular system and others, including cancer. Because *C. californicus* preys heavily on worms in the wild, a battery of novel toxins active against worms are provided. Such peptides have great potential in disease and pest control issues involving worms and worm-like organisms, e.g. schistozomes, trematodes, etc.

The total number of putative peptide toxins in the venom of *C. californicus* is large, and several important generalizations can be made. First, the extremely large number of isoforms of some individual classes of toxins, particularly calTx1.1 is unique to *C. californicus*. Second, the nature of the clustering of amino acid substitutions within a given family of toxins are often radical (e.g. charge changes), strongly suggesting that these clusters correspond to active surfaces of the peptide toxins that confer specificity for molecular targets. Third, the lack of strong congruence in cysteine-frameworks between the putative peptide sequences from *C. Californicus* and those of all other *Conus* thus far examined is the most significant unique feature.

The polypeptide sequences of the present toxins are provided in Table 1, SEQ ID NO:1-100, and may be set forth in the examples. The site for cleavage of the propeptides is shown, for example, in FIG. 4. Both propeptides and mature polypeptides are encompassed by the present invention, as well as polynucleotides encoding such polypeptides and propeptides. The invention relates to relatively short peptides, of at least about 20, at least about 30, at least 40, at least about 50 amino acid residues in length, which are naturally available in minute amounts in the venom of the cone snails or analogous to the naturally available peptides, and which preferably include multiple disulfide bonds. The conotoxins, as described herein, are useful for as pharmacologic agents, and may be provided in combination with a pharmaceutically acceptable excipient.

For use in the subject methods, any of the native mature conotoxin forms, modifications thereof, or a combination of forms may be used. Peptides of interest include fragments of at least about 12 contiguous amino acids, more usually at least about 20 contiguous amino acids, and may comprise 30 or more amino acids, up to the provided mature peptide, and may extend further to comprise other sequences present in the precursor protein. A fragment of a conotoxin peptide may be selected to achieve a specific purpose. For example, fragments may comprise a truncation, which can extend from residue 1 through 10 of the mature peptide from either the amino or the carboxy terminus, and may further delete additionally amino acids at residues 11, 12 or more.

Contoxins of interest include, without limitation, conotoxins of the CalTx1.1 family, for example as exemplified by SEQ ID NO:1-SEQ ID NO:21. The polypeptide sequences depicted in Table 1, are optionally cleaved between amino acid residue corresponding to 42 and 43 in SEQ ID NO:1, (for example cleaving TR↓DV). As used herein, the term "mature toxin" refers to polypeptides cleaved at this corresponding position. In some embodiments of the invention, a polypeptide of interest comprises a mature CalTx1.1 conotoxin.

In some embodiments, a conotoxin of interest comprises an amino acid sequence having at least about 95% sequence identity, at least about 90% sequence identity; at least about 85% sequence identity; or at least about 70% sequence identity with a sequence of the CalTx1.1 family, as provided herein, including a mature toxin sequence. Sequences of interest may comprise about 1, 2, 3, 4, 5, 6 or more amino acid substitutions, insertions or deletions relative to any one of the provided CalTx1.1 family sequences, where such sequences include specifically a mature toxin sequence. For example, a polypeptide of interest may have at least about 70% sequence identity to the mature toxin of SEQ ID NO:1, i.e. SEQ ID NO:1, residues 43-87; at least about 80% sequence identity to the mature toxin of SEQ ID NO:1, at least about 90% sequence identity to the mature toxin of SEQ ID NO:1; at least about 95% sequence identity to the mature toxin of SEQ ID NO:1.

Contoxins of interest also include, without limitation, conotoxins of the CalTx1.2 family, for example as exemplified by SEQ ID NO:22-SEQ ID NO:29. The polypeptide sequences depicted in Table 1, are optionally cleaved between amino acid residue corresponding to 42 and 43 in SEQ ID NO:22, (for example cleaving AR↓GV). As used herein, the term "mature toxin" refers to polypeptides cleaved at this corresponding position. In some embodiments of the invention, a polypeptide of interest comprises a mature CalTx1.2 conotoxin.

In some embodiments, a conotoxin of interest comprises an amino acid sequence having at least about 95% sequence identity, at least about 90% sequence identity; at least about 85% sequence identity; or at least about 70% sequence identity with a sequence of the CalTx1.2 family, as provided herein, including a mature toxin sequence. Sequences of interest may comprise about 1, 2, 3, 4, 5, 6 or more amino acid substitutions, insertions or deletions relative to any one of the provided CalTx1.2 family sequences, where such sequences include specifically a mature toxin sequence. For example, a polypeptide of interest may have at least about 70% sequence identity to the mature toxin of SEQ ID NO:22, i.e. SEQ ID NO:22, residues 43-84; at least about 80% sequence identity to the mature toxin of SEQ ID NO:22, at least about 90% sequence identity to the mature toxin of SEQ ID NO:22; at least about 95% sequence identity to the mature toxin of SEQ ID NO:22.

Contoxins of interest also include, without limitation, conotoxins of the CalTx2.1, 2.2, 2.3 or 2.4 family, for example as exemplified by SEQ ID NO:30-SEQ ID NO:36; and SEQ ID NO:76-83. The polypeptide sequences depicted in Table 1, are optionally cleaved at an arginine residue between amino acids 55 and 70. As used herein, the term "mature toxin" refers to polypeptides thus cleaved. In some embodiments of the invention, a polypeptide of interest comprises a mature CalTx2.1, 2.2 or 2.3 conotoxin.

In some embodiments, a conotoxin of interest comprises an amino acid sequence having at least about 95% sequence identity, at least about 90% sequence identity; at least about 85% sequence identity; or at least about 70% sequence identity with a sequence of the CalTx2.1, 2.2 or 2.3 family, as provided herein, including a mature toxin sequence. Sequences of interest may comprise about 1, 2, 3, 4, 5, 6 or more amino acid substitutions, insertions or deletions relative to any one of the provided CalTx2.1, 2.2 or 2.3 family sequences, where such sequences include specifically a mature toxin sequence. For example, a polypeptide of interest may have at least about 70% sequence identity to the mature toxin of SEQ ID NO:30; at least about 80% sequence identity to the mature toxin of SEQ ID NO:30, at least about 90% sequence identity to the mature toxin of SEQ ID NO:30; at least about 95% sequence identity to the mature toxin of SEQ ID NO:30.

Contoxins of interest also include, without limitation, conotoxins of the CalTx7 family, for example as exemplified by SEQ ID NO:91; of the CalTx3 family, as exemplified by SEQ ID NO:73; of the Tx9 family, as exemplified by SEQ ID NO:99-10; and additionally the toxins set forth in SEQ ID NO:37-72; SEQ ID NO:74; SEQ ID NO:84-90; and SEQ ID NO:92-99. The polypeptide sequences are depicted in Table 1. In some embodiments, a conotoxin of interest comprises an amino acid sequence having at least about 95% sequence identity, at least about 90% sequence identity; at least about 85% sequence identity; or at least about 70% sequence identity with a sequence of the a member of these family, as provided herein, including a mature toxin sequence. Sequences of interest may comprise about 1, 2, 3, 4, 5, 6 or more amino acid substitutions, insertions or deletions relative to any one of the provided sequences, where such sequences include specifically a mature toxin sequence.

The toxins are well-known to have a variety of post-translational modifications, in which the following equivalents may be made: Glu or γ-carboxy-Glu (Gla); pro or hydroxy-Pro; pTyr, mono-halo-Tyr, di-halo-Tyr, O-sulpho-Tyr, O-phospho-Tyr or nitro-Tyr; pLys, N-methyl-Lys, N,N-dimethyl-Lys or N,N,N-trimethyl-Lys. His residues may be substituted with halo-His; Arg residues may be substituted by Lys, ornithine, homoargine, N-methy-Lys, N,N-dimethyl-Lys, N,N,N-trimethyl-Lys or any unnatural basic amino acid (such as N-1-(2-pyrazolinyl)-Arg); the Lys residues may be substituted by Arg, ornithine, homoargine, N-methy-Lys, N,N-dimethyl-Lys, N,N,N-trimethyl-Lys or any unnatural basic amino acid (such as N-1-(2-pyrazolinyl)-Arg); and the Tyr residues may be substituted with any unnatural hydroxy containing amino acid (such as 4-hydroxymethyl-Phe, 4-hydroxyphenyl-Gly, 2,6-dimethyl-Tyr and 5-amino-Tyr). The C-terminus may contain a carboxyl or amide group. The Asn residues may be modified to contain an N-glycan and the Ser and Thr residues may be modified to contain an O-glycan, where glycan may mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1-.

Pairs of Cys residues may be replaced pairwise with isoteric lactam or ester-thioether replacements, such as Ser/(Glu or Asp), Lys/(Glu or Asp) or Cys/Ala combinations. Sequential coupling by known methods allows replacement of native Cys bridges with lactam bridges. The present invention is further directed to derivatives of the above peptides and peptide derivatives which are acylic permutations in which the cyclic permutants retain the native bridging pattern of native toxin.

The sequence of the conotoxin polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 276:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Also included in the present invention are functional derivatives of the provided polypeptide sequences. The term "functional derivative" refers to a fragment, conjugate or mutant derived from a gene or protein of interest, or combinations thereof, wherein a "fragment" is an isolated nucleic acid or polypeptide, respectively, that is derived from the gene or protein of interest. A "mutant" is a gene or protein having a sequence in which one or more nucleotides or amino acid residues, respectively, has been altered relative to the sequence of gene or protein of interest, or a sequence wherein one or more nucleotides or amino acids have been inserted into or deleted from the sequence of gene or protein of interest. Such derivatives (a) retain one or more utilities, biochemical or biological functions of the gene or protein of interest or (b) are capable of enhancing, modulating or inhibiting one or more utilities, biochemical or biological functions of the gene or protein of interest.

Fragments may be obtained directly, for example, by cleaving a gene with a restriction enzyme and isolating a specific restriction fragment derived from the gene, or indirectly, for example, by choosing a portion of the nucleotide sequence of a gene (or the amino acid sequence of a protein) and chemically synthesizing an oligonucleotide (or polypeptide) having that sequence.

For a protein, functional derivatives include but are not limited to synthetic polypeptides comprising an amino acid sequence derived from the protein of interest; mutant proteins, including dominant-negative mutants (Sheppard (1994) *Am. J. Respir. Cell. Mol. Biol.* 11:1-6); fusion proteins, a type of conjugate wherein a polypeptide having an amino acid sequence derived from the protein of interest is contiguous with one or more polypeptides having amino acid sequences derived from proteins other than the protein of interest; and other conjugates, such as those wherein the protein of interest or a fragment derived therefrom is structurally linked (chemically bonded) to one or more non-proteinaceous chemical moieties.

For a gene, functional derivatives include but are not limited to mutant nucleic acids; nucleic acids encoding fusion proteins; probes, including synthetic oligonucleotides such as PCR primers; antisense (reverse complement) nucleic acids, including ribozymes and synthetic oligonucleotides; molecular decoys, i.e., double-stranded nucleic acids capable of binding genetic regulatory factors by virtue of having a nucleotide sequence that is recognized by such factors; and conjugates, i.e., molecules wherein the gene of interest or a fragment derived therefrom is structurally linked (chemically bonded) to one or more chemical moieties, wherein such chemical moieties are not naturally occurring nucleic acids.

A "conjugate" is a gene, protein or fragment thereof that is chemically linked to a molecular entity that is not a part of the gene or protein of interest. As will be appreciated by those skilled in the art, conjugates may have the useful property of combining, in a single molecular entity, (a) one or more utilities, biochemical or biological functions of the gene or protein of interest with (b) the chemical, physical or biological properties of the chemical moieties structurally linked thereto.

A polynucleotide sequence encoding a conotoxin may be a complete coding sequence or a fragment thereof. Conventional codon usage may be used in the design of such polynucleotides, based on the known correlation between polynucleotide sequence and polypeptide sequence. The term "conotoxin gene" shall be intended to mean the open reading frame encoding specific conotoxin polypeptides, as well as adjacent 5' and 3' non-coding nucleotide sequences involved in the regulation of expression, up to about 1 kb beyond the coding region, but possibly further in either direction. A conotoxin gene, may be introduced into an appropriate vector for extrachromosomal maintenance or for integration into the genome of the host cell or organism.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The conotoxin genes are isolated and obtained in substantial purity, generally as other than an intact chromosome. Usually, the DNA will be obtained substantially free of other nucleic acid sequences that do not include a conotoxin sequence or fragment thereof, generally being at least about 50%, usually at least about 90% pure and are typically "recombinant," i.e. flanked by one or more nucleotides with which it is not normally associated on a naturally occurring chromosome.

The DNA sequences are used in a variety of ways. They may be used as probes for identifying conotoxin related genes. Homologs may have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J. Mol. Biol.* 215:403-10.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. At low stringency hybridization and washing conditions, nucleic acids with a degree of similarity to a nucleic acid encoding a Fzo homolog as low as 30% can be identified. Sequence identity may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. At high stringent hybridization and washing conditions, only the genes with a similarity to the probe DNA higher than 80% will be identified. These high stringent conditions consist of an overnight hybridization at 68° C. in a variety of buffers (Ausubel et al., eds., *Current Protocols in Molecular Biology,* 1988), followed by 2 washes of 10 min each at 68° C. in 2× standard saline citrate, SSC/0.1% SDS, one wash of 10 min at 68° C. in 1×SSC/0.1% SDS, and one wash of 5 min at 68° C. in 0.1×SSC/0.1% SDS).

The sequence of a conotoxin gene, including flanking promoter regions and coding regions, may be mutated in various ways known in the art to generate targeted changes in sequence of the encoded protein, etc. The DNA sequence or product of such a mutation will be substantially similar to the sequences provided herein, i.e. will differ by at least one nucleotide or amino acid, respectively, and may differ by at least two but not more than about ten or twenty nucleotides or amino acids. The sequence changes may be substitutions, insertions or deletions. Deletions may further include larger changes, such as deletions of a domain or exon. Other modifications of interest include epitope tagging, e.g. with the FLAg system, HA, etc.

Techniques for in vitro mutagenesis of cloned genes are known. Examples of protocols for site specific mutagenesis may be found in Gustin et al, *Biotechniques* 14:22 (1993); Barany, *Gene* 37:111-23 (1985); Colicelli et al, *Mol Gen Genet* 199:537-9 (1985); and Prentki et al, *Gene* 29:303-13 (1984). Methods for site specific mutagenesis can be found in Sambrook et al., *Molecular Cloning: A Laboratory Manual*, CSH Press 1989, pp. 15.3-15.108; Weiner et al, *Gene* 126:35-41 (1993); Sayers et al., *Biotechniques* 13:592-6 (1992), Jones and Winistorfer, *Biotechniques* 12:528-30 (1992); Barton et al., *Nucleic Acids Res* 18:7349-55 (1990); Marotti and Tomich, *Gene Anal Tech* 6:67-70 (1989); and Zhu, *Anal Biochem* 177:120-4 (1989).

Such mutated genes may be used to study structure-function relationships of conotoxins, or to alter properties of the protein that affect its function or regulation.

The subject gene may be employed for producing all or portions of the conotoxin protein, or functional derivatives (such as fusion proteins) of conotoxin proteins. For expression, an expression cassette may be employed. The expression cassette will provide a transcriptional and translational initiation region, which may be inducible or constitutive, where the coding region is operably linked under the transcriptional control of the transcriptional initiation region, and a transcriptional and translational termination region wherein these regions are functional in the host cell of choice. These control regions may be native to a conotoxin gene, or may be derived from exogenous sources.

The expression cassette may be integrated into the genome of a host cell, or may be part of an autogenously replicating expression construct that also comprises an origin of replication and a selectable marker such as, for example, a gene that encodes a function that confers resistance to an agent that would otherwise kill or prevent the growth of the host cell (e.g., for bacterial hosts, antibacterial agents such as ampicillin, tetracycline, kanamycin, streptomycin, chloramphenicol and neomycin; for eukaryotic hosts, cytotoxic agents such as G418, blasticidin, hygromycin and Zeocin™). The peptide may be expressed in prokaryotes or eukaryotes in accordance with conventional ways, depending upon the purpose for expression. For large scale production of the protein, a unicellular organism, such as *E. coli, B. subtilis, S. cerevisiae*, etc., may be used as the expression host cells.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The compounds of this invention can be incorporated into a variety of formulations for therapeutic administration. Particularly, conotoxin polypeptides and analogs thereof are formulated for administration to patients for modulation of activities blocked or enhanced byt he conotoxin. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The conotoxin may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are wellknown in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of infection, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 mg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the above described formulations, conotoxin or derivatives therefrom may be synthesized and stored as a solid lyophilized powder which is reconstituted into a pharmaceutically acceptable liquid immediately prior to use. Such formulations are usually preferred because it is recognized by those skilled in the art that lyophilized preparations generally maintain pharmaceutical activity better over time than their liquid counterparts.

In addition, conotoxins and their analogs could be applied topically on the skin as well as administered as aerosal sprays.

Alternatively, the peptides may be formulated as a liquid, e.g. comprising a buffer at a concentration of from about 1 mM to about 50 mM that functions to maintain the pH, wherein the anion of said buffer may be selected from the group consisting of acetate, phosphate, carbonate, succinate, citrate, borate, tartrate, fumarate and lactate; and an alcohol which may be selected from the group consisting of mannitol, sorbitol, ribotol, arabitol, xylitol, inositol, galactitol, methanol, ethanol and glycerol. Other additives may include amino acids such as methionine, arginine, lysine, glutamic acid, cysteine, glutathione, and the like, where amino acids are generally present in concentrations ranging from about 1 mM to about 100 mM. Various sugars are optionally included in the formulations, including, for example, glucose, sucrose, lactose, fructose, trehalose, mannose, and the like. Additive sugars are generally present in concentrations ranging from about 1% to about 10%.

In one embodiment, the polypeptides described herein are used as neuromuscular blocking agents in conjunction with surgery or for intubation of the trachea by conventional parenteral administration e.g., intramuscular or intravenous administration in solution. Thus, the present invention relates to a method for treating a patient during surgical procedures requiring anesthesia and musculoskeletal relaxation. In particular, the method comprises administering to the patient an amount of a compound effective for providing relaxation of muscle. The method involves administering an effective amount of a conotoxin polypeptide of the invention. The present invention relates to a pharmaceutical composition incorporating a compound described herein or its pharmaceutically acceptable salts.

Exemplary methods for administering such muscle relaxant compounds (e.g., so as to achieve sterile or aseptic conditions) will be apparent to the skilled artisan. Certain methods suitable for administering compounds useful according to the present invention are set forth in Goodman and Gilman's The Pharmacological Basis of Therapeutics, 7th Ed. (1985). The administration to the patient can be intermittent; or at a gradual, continuous, constant or controlled rate. Administration can be to a warm-blooded animal (e.g. a mammal, such as a mouse, rat, cat, rabbit, dog, pig, cow or monkey); but advantageously is administered to a human being. Administration occurs after general anesthesia is administered. The frequency of administration normally is determined by an anesthesiologist, and typically varies from patient to patient.

The dose of the compound is that amount effective to provide a desired effect for a desired time frame. By "effective amount" or "effective dose" is meant that amount parenterally administered (e.g., injected intravenously) sufficient to bind to relevant receptor sites on the musculoskeletal fiber of the patient, and to elicit neuropharmacological effects (e.g., elicit brief depolarization, thus resulting in effective short duration relaxation of skeletal muscle). Short duration typically ranges from about 5 to about 60 minutes.

An effective amount of the compound administered to a patient provides rapid onset and short-lived muscle relaxation. For adult human patients undergoing short surgical procedures, the effective dose of typical compounds injected intravenously generally is from about 0.001 mg/kg to about 0.8 mg/kg body weight, preferably from about 0.05 mg/kg to about 0.5 mg/kg, and more preferably from about 0.05 mg/kg to about 0.3 mg/kg. Following administration of typical compounds in such a concentration range, the onset of paralysis normally develops within 1 to 2 minutes, and is reversible (i.e., muscle tone returns within a short period of time). The compounds of this invention would normally be readministered every 15 to 30 minutes after initial administration or given as a slow continuous infusion depending upon the length of time a muscular block is desired, and as determined by the anesthetist and surgeon in charge of the patient. For adult human patients undergoing long surgical procedures, the effective dose of typical compounds is administered through continuous or intermittent intravenous perfusion at a rate from about 0.001 mg/min to about 0.8 mg/min, preferably from about 0.01 mg/min to about 0.5 mg/min, and more preferably from about 0.01 to about 0.25 mg/min. Following administration of typical compounds in the specified amounts, the onset of paralysis typically develops within 1 to 2 minutes and persists for the duration of the superfusion.

For human patients in the pediatric population undergoing short surgical procedures, the effective dose of typical compounds injected intravenously generally is from about 0.001 mg/kg to about 0.5 mg/kg body weight, preferably from about 0.01 mg/kg to about 0.4 mg/kg, and more preferably from about 0.01 mg/kg to about 0.25 mg/kg. Following administration of typical compounds in such a concentration range, the onset of paralysis normally develops within 1 to 2 minutes, and persists for a short period of time before recovery is achieved. For infants and children undergoing long surgical procedures, the effective dose of typical compounds is administered through continuous or intermittent intravenous perfusion at a rate from about 0.001 mg/min to about 0.5 mg/min, preferably from about 0.005 mg/min to about 0.3 mg/min, and more preferably from about 0.005 mg/min to about 0.2 mg/min. The total amount of drug administered using such a parenteral route of administration generally does not exceed a total of 10 mg, often does not exceed 5 mg and frequently does not exceed 2 mg. Following administration of typical compounds in the specified amounts, the onset of paralysis typically develops within 1 to 2 minutes and persists for the duration of the superfusion.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Identification and Characterization of a Novel Peptide Toxin from conus californicus Sodium channel-blocking activity of C. californicus venom. Individual venom glands were dissected, and the muscular bulbs and proximal portion of the venom duct were discarded. Crude venom was removed from the long, distal portion of the duct by manually squeezing out the contents onto a small piece of plastic film. This material was suspended in 0.5 ml of the external solution to be used for voltage-clamp experiments, manually homogenized, and then heated to 90° C. for 5 min to eliminate protease and phospholipase activity. Without this treatment, deleterious effects on cells were observed even at fairly low dilutions. The sample was then centrifuged at 14,000 rpm for 15 min, and the crude duct venom supernatant was decanted and stored in frozen aliquots.

Milked venom was obtained by enticing a live snail to attack a target of fresh squid (*Loligo opalescens*) skin stretched over an open 0.5 ml microfuge tube. A single injection yielded about 5-10 μl of fluid, but it is unclear how much of this is seawater. This material was immediately frozen and later diluted into external solution for physiological recordings.

Conventional whole-cell recordings were carried out on squid (*Loligo opalescens*) giant fiber lobe (GFL) neurons to record Na currents ($I_{Na}$) as previously described (Gilly et al 1997; 1990). Some experiments were also carried out using the same methods on presumptive motoneurons from stellate ganglia of *Sepia officianalis* and *Octopus rubescens* and from pedal ganglia of *Aplysia californica*, and *Strombus luhuanus*. Cells were maintained in culture as previously described, except glass cover-slips were used for plating cells, the temperature was reduced to 12° C., and the medium contained 5 mM treahlose at pH 8.0.

Tests of duct venom or milked venom showed no large or consistent effects on K currents recorded from squid GFL neurons following previously described procedures (Mathes et al., 1997). Similarly, no consistent effect was detected on non-inactivating putative P-type Ca channels in this preparation (McFarlane and Gilly, 1996). In contrast to these results, voltage-dependent Na currents ($I_{Na}$) were found to be quite sensitive to both duct and milked venoms. Both venoms reduce $I_{Na}$ without significant alteration of its time-course and are partially reversible.

Purification of a Na channel-blocking peptide from duct venom. Crude venom was removed from 10 ducts, suspended in 0.1% trifluoroacetic acid (TFA) plus 5% acetonitrile (MeCN) in distilled water, manually homogenized and centrifuged as described above. The supernatant was collected, and the pellet was re-suspended in 0.1% TFA plus 25% MeCN, and the extraction, centrifugation and supernatant removal repeated. This cycle was repeated with sequentially higher concentrations of MeCN (50,75 and 99.9%), and all supernatant material was pooled in a final volume of 1000 µl. This 'duct venom stock' was used for purification by Reverse-Phase High Performance Liquid Chromatography (RP-HPLC) in collaboration with Dr. J. P. Bingham and for subsequent bioassays by whole-cell patch clamp.

Fraction 5 was subjected to a second round of RP-HPLC separation using analytical methods, and at least nine distinct peaks were evident. These nine sub-fractions were dried for storage. In order to carry out bioassays, each of these samples was taken up in 20 µl of 50% MeCN, evaporated to 5 µl volume and then added to 400 µl external recording solution. These samples were finally tested following an additional 4-fold dilution. A high level of Na-channel blocking activity was found only in sub-fraction 8 (55% block). This material reversibly blocked $I_{Na}$ in the same way as both duct and milked venoms did. HPLC analysis revealed that sub-fraction 8 contained only a single elutable peak, and we henceforth refer to this purified material as calTx (or more precisely, calTx1.1; see also below).

All other individual sub-fractions tested (5,6,7,9) had blocking activity of 5% or less. Pooled material from sub-fractions 1-4 (i.e., each present at the standard dilution) showed blocking activity of 25-30%, but these sub-fractions have not yet been investigated in detail.

Chemical analysis of sub-fraction 8. This two-step RP-HPLC separation and accompanying bioassays were carried out twice with similar results. This material has been used for carrying out N-terminal sequencing and for detailed physiological experiments.

Material from the first purification was used primarily for carrying out conventional Edman-degradation, N-terminal sequencing (PAN Facility, Stanford Univ). This unambiguously identified the first 20 aa of the calTx peptide sequence with the exception of aa 17 (FIG. 1. A blank cycle at this position (also at 21) is suggestive of post-translational modification, many of which have been described in *Conus* peptides. Although sequencing continued for at least 12 cycles, the low signal to noise ratio compromised unaided (see below) identification beyond Gln at position 20.

In order to deduce the rest of the sequence of the calTx peptide, we employed a conventional, degenerate reverse-transcription PCR approach to obtain the corresponding genetic sequence. A degenerate antisense (reverse) primer (calTX1.1 rev) was designed based on the partial calTx peptide sequence (FIG. 1), and the sense primer (calTx1.1 F1) was made to match a highly conserved signal sequence present in many *Conus* venom peptide sequences (Duda and Palumbi, 1999; Woodward et al., 1990). RNA was extracted from 12 venom ducts (venom first removed), cDNA was synthesized using reverse transcriptase, and PCR was used to successfully amplify the propeptide and N-terminal coding region of the mature calTx peptide (FIG. 1). This product was subcloned and sequenced. Exact forward primers (calTx1.1 F2 and calTx1.1 F3) were then designed based on this information and used in 3' RACE reactions of oligo-dT primed cDNA to amplify the remainder of the coding and 3' untranslated regions of calTx. These products were also subcloned and sequenced. The predicted aa sequence for the entire propeptide and mature toxin coding regions of calTx are depicted in FIG. 1. Being the first putative peptide sequence identified from *C. californicus*, we renamed calTx as calTx1.1, and following further identification of additional isoforms as calTx1.1 A (see below).

CalTx1.1A is very acidic and has a novel cysteine framework, the N-terminal region of which is unknown in any other *Conus* peptides known to target Na channels (µ, µO, or δ) and thus appears to represent a new family. The C-terminal portion of calTx1.1A shows a cysteine arrangement generally similar to a broad group of toxins that block or modulate a variety of voltage-gated ion channels ($Na_v$: µ, µO, δ), $K_v1$: κ, $Ca_v$: ω; see FIG. 2). The mature peptide begins following an arginine residue in the propeptide region, which is a common site for proteolytic processing of *Conus* peptides (Craig et al., 1999). Tentative calls for aa 21-32 in the Edman sequencing were in agreement with this predicted sequence A blank Edman cycle at aa 23 suggests that hydroxy-proline is present at this position (predicted to be proline by cDNA).

In addition, sequences encoding other families of venom peptides were obtained using the calTx1.1 F1 primer (FIG. 1) in 3' RACE reactions of oligo-dT primed *C. californicus* cDNA. The mature toxin amino acid sequences for two six-cysteine, four-loop venom peptides (calTx 2.1 and calTx2.2) and a four-cysteine, two-loop peptide (calTx3.1) are given in Table 1. These sequences are similar in cysteine framework to a variety of venom peptides previously identified in other *Conus* species (Jones and Bulaj, 2000), but as described below are not identifiable with any known class of toxins from the other species.

Figure 3:
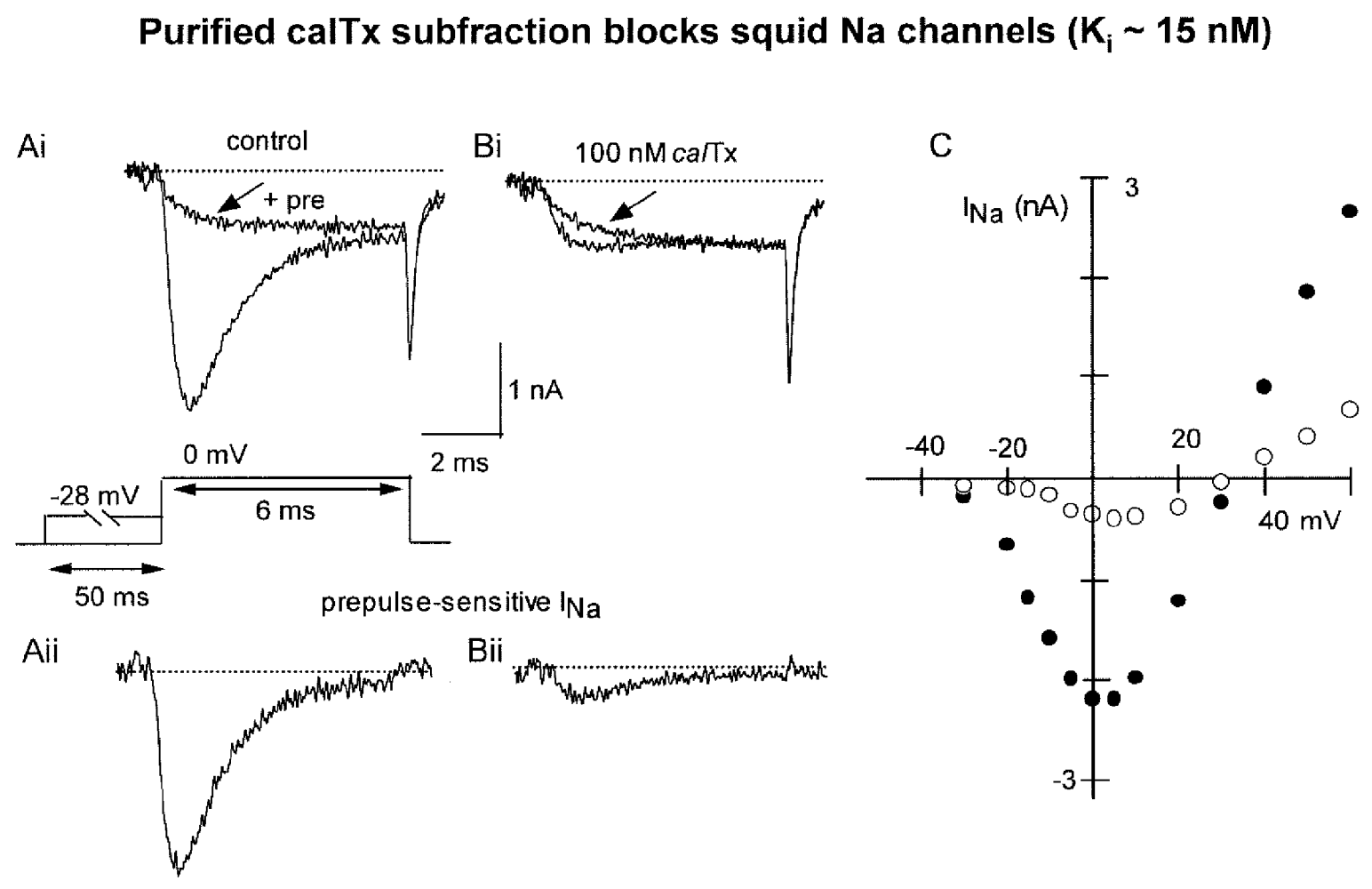

Physiological experiments with purified calTx (calTx1.1A). Although the conditions used for our whole-cell recordings eliminate K currents, a significant amount of non-inactivating Ca current ($I_{Ca}$) persists (FIG. 3Ai). A prepulse-method was therefore used to separate $I_{Na}$ to allow a more detailed study of the blocking action of calTx. The prepulse (50 ms duration to ~−30 mV removes essentially all inactivating $I_{Na}$ (traces marked with arrows in FIG. 3Ai) with minimal effect on $I_{Ca}$ (Gilly et al, 1997). Subtraction of these records yields the prepulse-sensitive $I_{Na}$ displayed in FIG. 3Aii. Typically, about 15% of TTX-sensitive $I_{Na}$ in cultured GFL neurons is non-inactivating (Gilly and Brismar, 1989), and this relatively minor component was therefore not included in our analysis of the effects of calTx on prepulse-sensitive $I_{Na}$.

FIG. 3Bi illustrates the effect of a dose of purified calTx1.1A estimated to be 100 nM. The time course of the residual prepulse-sensitive $I_{Na}$ in calTx is not significantly different than normal (FIG. 3Bii)l. FIG. 3C plots prepulse-sensitive $I_{Na}$ vs. test-pulse voltage from this same cell in the absence (●) and presence (○) of 100 nM calTx. Block is nearly voltage-independent, with potency decreasing e-fold in 300-400 mV. Steady-state voltage-dependence of fast inactivation of the residual $I_{Na}$ in calTx is also not significantly affected.

Dose-response data for calTx were analyzed for prepulse-sensitive $I_{Na}$ at 0 mV in a number of cells using the same purified material. These data were consistent with 1:1 binding of calTx. by a Na channel and indicate a $K_i$ of ~15 nM.

Identification of "full-length" calTx1.1 PCR products: Primers were Albert (=calTx1.1F3) designed from partial sequence above and oligo-dT. Sequence of the N-terminal region of the leader sequence is ambiguous, because of calTx1.1F1 primer used in original amplification. No independent 5' UTR sequence is available. Additional CalTx1.1 sequences were identified via PCR as described below, and this start sequence has been confirmed. A summary of the strategy is shown in FIG. 7.

The forward primer initially used in this work (calTx1.1F1) also successfully amplified four other sequences early in the research program, which we called calTx2.1, 2.2 and 3.1. Thus, there is a grouping of putative peptides that are characterized by the MKLT motif and the translation start site. MKLT is also a motif found in the toxin classes identified in FIG. 2, but there is no other apparent sequence homology with *C. californicus.* cDNA library from *C. californicus* venom ducts: RNA was extracted from 12 squeezed venom ducts and pooled. 12 μg of RNA was used in mRNA purification based on oligo dT column. 0.12 μg of mRNA was then used for cDNA synthesis using reverse transcriptase. This cDNA was then ligated into Invitrogen pSport1 plasmid as indicated, plated, and random colonies were mini-prepped and sequenced using a T7 primers. Sequences thus identified constitute the "clone" series (Cl nomenclature on spreadsheets).

Additional sequences were generated from this library via PCR amplification of individual clones using Taq polymerase with M13 and M15 (or T7) primers. PCR products were then purified using WizardPrep kit ("Wizard prep" series=WP nomenclature on spreadsheet) and sequenced.

Once a new sequence was identified in above manner, exact primers were designed that were analogous to either Albert or calTx1.1F and used with 3' utr primer in PCR with Pfu from cDNA. Initial PCR products were cloned into "PCR4 Blunt TOPO" using the Zero Blunt TOPO PCR cloning kit. Clones thus obtained were amplified with Taq and M13F/M13R primer, and the products were purified using Qiaquick kit. These final products were then sequenced using both T3 and T7 primers. These products constitute the Qiagen (Q)-nomenclature series in the tables. This same procedure was used to amplify sequences from invidiual snails (see below).

CalTx1 series sequences. calTx1.1: calTx1.1A was originally identified as described above. Additional variants were obtained via PCR amplifications in the Qiagen series (12 snails pooled and 16 individual snails). A total of 19 additional calTx1.1 variants were identified, which are named calTx1.1 B-U. The coding regions for these putative calTx1.1 peptides are given in FIG. 4. Based on amplifications and cloning from individual snails, it appears that the most common mRNAs in the venom duct of *C. californicus* (and presumably peptide isoforms in the venom) are calTx1.1 A, B, F, U and N.

Patterns of amino acid substitutions in the calTx1.1A family are significant. A high degree of variability exists only at certain positions, and often these involve radical changes such as substitution of a small amino acid for a larger, charged one (position 8: G→D or E; position S→D or E), a charge reversal (position 20: E or R) or substitution of a charged residue by a more hydrophobic one (position 36: R and W). Furthermore, these positions of high diversity tend to be clustered between specific Cys residues—C1-C2, C4-C5 and C7-C8. In contrast, amino acids between C2 and C3 are completely conserved in all calTx1.1 members, and substitutions between C6-C7 and from C8 to the C terminus tend to more conservative.

These patterns strongly resemble those that have been identified in peptide toxins that block Kv1 channels that are found in various scorpion species (charybdotoxin family). Mutagenesis studies have revealed that these variable amino acids tend to confer specificity to particular Kv1 channel isoforms, which also have highly diverse regions in extracellular loop domains.

CalTx1.2. A family of sequences closely related to calTx1.1 was obtained from the library sequencing-screen (clone 68) and named calTx1.2. A second variant was obtained via plasmid PCR from library—wp31. 5 additional variants were obtained by PCR from cDNA as with calTx1.1. These sequences are compared to that of calTx1.1A in FIG. 5.

Based on the dispositions of the Cys resisdues, CalTx1.2 family is clearly related to the CalTx1.1 family. However, there is no amino acid sequence homology in either the toxin-coding region or in the leader/prohormone region. Discovery of this additional calTx1 family is significant, because of the novelty of this group of sequences with those from other *Conus* species.

CalTx2 series and others. calTx2.1 and 2.2 were obtained by PCR (CTX2F and oligo-dT primers) as described above. Clone G was obtained by sequencing and was named calTx2.3. Many variants of calTx2.3 were obtained by PCR from cDNA using primers non-degenerate exact primers analogous to "Albert" (forward) and 3' UTR (reverse). These sequences share a general 6-cysteine framework with toxins indicated in FIG. 2 other than calTx1.1, but total lack of amino acid or nucleotide homology with any known toxins from these families prevents identifying any of the calTx2 members with these established families.

A large number of other sequences were also obtained in an analogous manner that encode putative toxins containing 4, 6 or 8 cysteine residues. FIG. 6 presents a summary of the numbers of families identified and the numbers of members found in each to date.

A tabulation of the sequences of interest is provided in Table 1.

TABLE 1

| Name | SEQ ID | Polypeptide Sequence |
|---|---|---|
| | | 10 20 30 40 50 |
| calTx1.1A | 1 | MKLTCVLVVL LLLLPYGDLI TNNYIRGAAR KVTPWRRNLK TRDVCDSLVG |
| calTx1.1B | 2 | MKLTCVLVVL LLLLPYGDLI TNNYIRGAAR KVTPNRRNLK TRDVCDSLVG |

TABLE 1-continued

| ID | # | Sequence |
|---|---|---|
| calTx1.1C | 3 | MKLTCVLVVL LLLLPYGDLI TNNYIRGAAR KVTPWRRNLK TRDVCDSLVG |
| calTx1.1D | 4 | MKLTCVLVVL LLLLPYGDLI TNNYIRGAAR KVTPWRRNLK TRDVCDSLVE |
| calTx1.1E | 5 | MKLTCVLVVL LLLLPYGDLI TNNYIRGAAR KVTPWRRNIK TRDVCDSLVE |
| calTx1.1F | 6 | MKLTCVLVVL LLLLPYGDLI TNNYIRGAAR KVTPWRRNLK TRDVCDSLVD |
| calTx1.1G | 7 | MKLTCVLVVL LLLLPYGDLI TNNYIRGAAR KVTPWRRNLK TRDVCDSLVD |
| calTx1.1H | 8 | MKLTCVLVVL LLLLPYGDLI TNNYIRGAAR KVTPWRRNLK TRDVCESVAG |
| calTx1.1I | 9 | MKLTCVLVVL LLLLPYGDLI TNNYIRGAAR KVTPWRRNLK TRDVCDSLVD |
| calTx1.1J | 10 | MKLTCVLVVL LLLLPYGDLI TNNYIRGAAR KVTPWRRNLK TRDVCDSLVG |
| calTx1.1K | 11 | MKLTCVLVVL LLLLPYGDLI TNNYIRGAAR KVTPWRRNLK TRDVCDSLVG |
| calTx1.1L | 12 | MKLTCVLVVL LLLLPYGDLI TNNYIRGAAR KVTPNRRNLK TRDVCDSLVG |
| calTx1.1M | 13 | MKLTCVLVVL LLLLPYGDLI TNNYIRGAAR KVTPWRRNLK TRDVCDSLVD |
| calTx1.1N | 14 | MKLTCVLVVL LLLLPYGDLI TNNYIRGAAR KVTPWRRNLK TRDVCDSLVD |
| calTx1.1O | 15 | MKLTCVLVVL LLLLPYGDLI TNNYIRGAAR KVTPWRRNLK TRDVCDSLVG |
| calTx1.1P | 16 | MKLTCVLVVL LLLLPYGDLI TNNYIRGAAR KVTPWRRNLK TRDVCKK SP |
| calTx1.1Q | 17 | MKLTCVLVVL LLLLPYGDLI TNNYIRGAAR KVTPWRRNLK TRDVCDSLVE |
| calTx1.1R | 18 | MKLTCVLVVL LLLLPYGDLI TNNYIRGAAR KVTPWRRNLK TRDVCDSLVG |
| calTx1.1S | 19 | MKLTCVLVVL LLLLPYGDLI TNNYIRGAAR KVTPWRRNLK TRDVCDSLVG |
| calTx1.1T | 20 | MKLTCVLVVL LLLLPYGDLI TNNYIRGAAR KVTPWRRNLK TRDVCDSLVG |
| calTx1.1U | 21 | MKLTCVLVVL LLLLPYGDLI TNNYIRGAAR KVTPWRRNLK TRDVCDSLVD |
| calTx1.2 | 22 | MKLTCVLVVL LLVLPFGDLI TTSNTEDNKR GATPWQNSLK ARGVCSTPEG |
| wp57 | 23 | MKLTCVLVVL LLVLPFGDLI TTSNTEDNKR GATPWQNSLK ARGVCSTPEG |
| Q147 | 24 | MKLTCVLVVL LLVLPEGDLI TTSNTEDNKR GATPWQNSLK ARGVCSTPEG |
| Q60 | 25 | MKLTCVLVVL LLVLPEGDLI TTSNTEDNKR GATPWQNSLK ARGVCSTPEG |
| Q63 | 26 | MKLTCVLVVL LLVLPFGDLI TTSNTEDNKR GATPWQNSLK ARGVCSTPEG |
| Q68 | 27 | MKLTCVLVVL LLVLPFGDLI TTSNTEDNKR GATPWQNSLK ARGVCSTPEG |
| Q74 | 28 | MKLTCVLVVL LLVLPFGDLI TTSNTEDNKR GATPWQNSLK ARGVCSTPEG |
|  | 29 | MKLTCVLVVL LLVLPFGDLI TTSNTEDNKR GATPWQNSLK ARGVCSTPEG |
| calTx2.3 | 30 | MKLTTVLVVA LLVLAACQFT VTDNSGDDPE NPSLRSVGEN QNPDSTKTIT |
| Q32 | 31 | MKLTTVLVVA LLVLAACQFT VTDNSGDDPE NPSLRSVGEN QNPDSTKTIT |
| Q40 | 32 | MKLTTVLVVA LLVLAACQFT VTDNSGDDPE NPSLRSVGEN QNPDSTKTIT |
| Q35 | 33 | MKLTTVLVVA LLVLAACQFT VTDNSGDDPE NPSLRSVGEN QNPDSTKTIT |
| Q33 | 34 | MKLTTVLVVA LLVLAACQFT VTDNSGDDPE NPSLRSVGEN QNPDSTKTIT |
| Q39 | 35 | MKLTTVLVVA LLVLAACQFT VTDNSGDDPE NPSLRSVGEN QNPDSTKTIT |
| Q40 | 36 | MKLTTVLVVA LLVLAACQFT VTDNSGDDPE NPSLRSVGEN QNPDSTKTIT |
|  | 37 | GAARKVTPWR RNLKTRDVCD SLVGGHCIHN GCWCDQEAPH GNCCDTDGCT |
|  | 38 | DNKRGATPWQ NSLKARGVC STPEGSCVHN GCICQNAPC CHPSGCNWAN |
|  | 39 | DNKRGATPWQ NSLKARGVCS TPEGSCIHNG CCQNAPQCCH PSGCNWANVCP |
|  | 40 | DNKRGATPWQ NSLKARGVCS TPEGSCIHNG CMCQNAPCC HPSGCNWANVC |
|  | 41 | DNKRGATPWQ NSLKARGVCS TPEGSCIHNG CCQNAPQCCH PSGCNWANVCP |

TABLE 1-continued

|  |  |  |
|---|---|---|
|  | 42 | DNKRGATPWQ NSLKARGVCS TPEGSCIHNG CCQNAPQCCH ASGCNWANVCP |
|  | 43 | DNKRGATPWQ NSLKARGVCS TPEGSCIHNG CCHNAPQCCH PSGCNWANVCP |
|  | 44 | DNKRGATPWQ NSLKARGVCS TPEGSCIHNG CCQNAPQCCH PSGCNWANVCP |
|  | 45 | DNKRGATPWQ NSLKARGVCS TPEGSCIHNG CCQNAPQCCH PSGCNWVNVCP |
|  | 46 | DDPENPSLR SVGENQNPDS TKTITAWATR DMTNMRRGLN RPSKRCLAGS |
|  | 47 | DDPENPSLR SVGENQNPDST KTITAWATRD MTNMRRGLNRP SKRCLAGSAR |
|  | 48 | DDPENPSLR SVGENQNPDST KTITAWATRD MTNMRRGLNRP SKRCLAGSAP |
|  | 49 | DDPENPSLR SVGENQNPDST KTITAWATRD MTNMRRGLSRP SKRCIAGGQP |
|  | 50 | DDPENPSLR SVGENQNPDST KTITAWATRD MTNMRRGLSRP SKRCIGGGDP |
|  | 51 | DDPENPSLR SVGENQNPDST KTITAWATRD MTNMRRGLNRP SKRCIGGGDP |
|  | 52 | DDPENPSLR SVGENQNPDST KTITAWATRD MTNMRRCLTRP SKRCLAGSAP |
|  | 53 | RAIASRLRP TKRHCGQNVCL MLAGQCCEEF WCIGYRCW |
|  | 54 | YPKWLRGLS TDXSERGCWLC LGPNACCRGS VCHNYCPR |
|  | 55 | YRKWRRSGT STGMRLGSRDC GPWCWGQNKC CPDSCRSLHESCT |
|  | 56 | DREWRDLEW LRSLKAHDKRA GCCPTIMYKT GACRTNRCR |
| wp9; | 57 | MRFYIGLMAA LMLTSVLRTD SASVGQTGTK SELAVIERVI RQRDAADVKP |
| cl 15 | 58 | MRFYIGLMAA LMLTSILRTD SASVGQTGTK SELALIERVI RQRDAADVKP |
| Q76 | 59 | MRFYIGLMAA LMLTSVLRTD SASVGQTGTK SELAVIERVI RQRDAADVKP |
| Q81 | 60 | MRFYIGLMAA LMLTSILRTD SASVDQTGAE GGLALIERVI RQRDAADVKP |
| wp1; | 61 | MKFLLFLSVA LLLTSFIETE AGPVNEAGVE RLFRALVGRG CPADCPNTCD |
| Q111 | 62 | MKFLLFLSVA LLLTSFIETE AGPVNEARVE RLFRALVGRG CPADCPNTCD |
| Q114 | 63 | MKFLLFLSVA LLLTIFIETE AGPVNEAGVE RLFRALVGRG CPADCPNTCD |
| Q115 | 64 | MKFLLFLSVA LLLTSFIETE AGPVNEAGVE RLFRALVG |
| wp 23 | 65 | MKLCVVIVLL MLAMPFNGGE ASRFFNQHAR SQRSGMKTRG IWCDPPCPKG |
| Q138 | 66 | MKLCVVIVLL MLAMPFNGGE ASRFFNQHAR SQRSGMKTRG IWCDPPCPEG |
| Q141 | 67 | MKLCVVIVLL MIAMPFNGGE ASRFFNQHAR SQRSGMKTRG IWCDPPCPEG |
| Q137 | 68 | MKLCVVLVLL MIAMPFNGGE ASRFFNQHAR SQRSGMKTRG IWCDPPCPEG |
| Q144 | 69 | MKLCVVIVLL MLAMPFNGGE ASRFFNQHAR SQRSGMKTRG IWCDPPCPDG |
| Q136 | 70 | MKLCVVIVLL MLAMPFNGGE ASRFFNQHAR SQRSGMKTRG IWCDPPCPEG |
| Q142 | 71 | MKLCVVIVLL MLAMPFNGGE ASRFFNQHAR SQRSGMKTRG TWCDPPCPEG |
| cl 37 | 72 | MMYCLPVVCI LLLLIPSSAT FVVESRLEKD QAQSFTGDAW KRVSPIHEMI |
| calTx 3.1 | 73 | MKLTCVFIIA VLILTACHFI VADDTGDREW RDLEWLRSLK AHDKRAGCCP |
| wp 10 | 74 | MKNELAKARA KACCPIIAMD RRGGNKLDLC CTFFPTFVLF S |
|  | 75 | MIIYKDKMSG EELFTDAFHV HEEETHMKFC GKLTLEKDSI DEKMFGGNAS |
| cl 163 |  | EYFKKLQEKK FPCPAEGEDK TEYDCKVKEF KKRAKGFFDF VLENHKDLCC |
| calTx 2.1 | 76 | MKLTCVIIIA ALILSISTAG GDIQKYRAIA SRLRPTKRHC GQNVCLMLAG |
| calTx 2.2 | 77 | VVTACQFTAA DDMEYPKWLR GLSTDXSERG CWLCLGPNAC CRGSVCHNYC |
| calTx 2.4 | 78 | VTACQFIAAD NTEYRKWRRS GTSTGMRLGS RDCGPWCWGQ NKCCPDSCRS |
| CalTx 2.3 | 79 | MKLTTVLVVA LLVLAACQFT VTDNSGDDPE NPSLRSVGEN QNPDSTKTIT |
| wp66 | 80 | MRFLHFPLIVA VLLASFMESG AMPRNPKKKR GWDTPAPCRY CQWNGPQCCV |

TABLE 1-continued

| Name | SEQ ID | Polypeptide Sequence |
|---|---|---|
| Q128 | 81 | MRFLHFLIVA VLLASFMESG AMPRNPKKKC CCCCCS |
| Q163 | 82 | MRFLHFLIVA VLLASFMESG AMPRNPKKKC CKCCCC |
| Q127 | 83 | MRFLHFLIVA VLLASFMESG AMPRNPKKKV CCCCCC |
| cl 81 | 84 | MTFLLLLVSV CMMATGEERT KRDVCELPFE EGPCFAAIRV YAYNAETGDC |
| WP54 | 85 | MNCYLILTVA LLLTSAMTGT TTAGQLNKKG VTLREDDGFP CNAGNCACLP |
| Q95 | 86 | MNCYLILTVA LLLTSAMTGT TTAGQLNKKR VTLREDDGFP CNAGNCACLP |
| Q85 | 87 | MNCYLILTVA LLLTSAMTGT TTAGQLNKKG VTLREDDRFP CNAGNCACLP |
| Q86 | 88 | MNCYLILTVA LLLTSAMTGT TTAGQLNKKG VTLREDDRFP CNAGNCACLP |
| Q90 | 89 | MNCYLILTVA LLLTSAMTGT TTAGQLNKKG VTLREDDRFP CNAGNCACLP |
| Q89 | 90 | MNCYLILTVA LLLTSAMTGT TTAGQLNKKG VTQREDDRTF PCNSGRCACQ |
| cal Tx 7 | 91 | MKFDGSLFLA ILLCITMTTK RTSARTCDYH DIIRVQYPDG RVLSGDYCYC DPSNGFEDPG MWCRCSTYSF FGNSRRWENS MW |
| calTx 1.1 | 92 | MKLTCVLVVL LLLLPYGDLI TNNYIRGAAR KVTPWRRNLK TRDVCDSLVG |
| calTx 1.2 | 93 | MKLTCVLVVL LLVLPFGDLI TTSNTEDNKR GATPWQNSLK ARGCSTPESC |
| wp31 | 94 | MMSTKGITLF LCLLLLALAT SVNCGQGTRR SRMTRALHGG RPSARYDAPY |
| Q18 | 95 | MMSTKGITLF LCLLLLALAT SVNGGQGTRR SRMTRALHGD RPSARYDAPY |
| Q21 | 96 | MMSTKGITLF LCLLLLALAT SVNGGQGTRR SRMTRALHGG RPSARYDAPY |
| Q23 | 97 | MMSTKGITLF LCLLLLALAT SVNGGQGTRR SRMTRALHGR YDAPYYDAPY |
| Q24 | 98 | MMSTKGITLF LCLLLLALAT SVNGGQCTRR SRMTRALHGG RPSARYDAPY |
| cal Tx9C | 99 | MKLLLTLLLG SALMCITLAD ECGLGTERPV KEVIDNVRTM YYCDCRAGDA KHDSSGDKPQ FYCSCLNYKY EQSHADSRYW TIRCYMGDIC D |
| cl 46-3 | 100 | MKLLLTLLLG SALMCITLAD ECGLGTHRPV KEVIDNVRTM YYCDCRAGDA |

| Name | SEQ ID | Polypeptide Sequence |
|---|---|---|
|  |  |         60          70          80 |
| calTw1.1A | 1 | GHCIHNGCWC DQEAPHGNCC DTDGCTAAWW CPGTKWD |
| calTw1.1B | 2 | GHCIHNGCWC DQDAPHGNCC DTDGCTAAWW CPGTKWD |
| calTw1.1C | 3 | GHCIHNGCWC DQEAPHGNCC NTSGCTARWW CPGTKFD |
| calTw1.1D | 4 | GRCIHNGCWC DEEAPEGNCC DTAGCTAWWW CPGTKWD |
| calTw1.1E | 5 | GRCIHNGCMC DEYSPHGNCC DTAGCTAWWW CPGTKWD |
| calTw1.1F | 6 | GRCIHNGCYC ERDAPNGNCC NTDGCTARWW CPGTRWD |
| calTw1.1G | 7 | GRCIHNGCYC ERDAPNENCC NTDGCTARWW CPGTKWD |
| calTw1.1H | 8 | RCIHNGCWCE RSAPHGNCCN TSGCTARWWC PGTKFD |
| calTw1.1I | 9 | GRCIHNGCFC ERSAPHGNCC NTSGCTVRWW CPGTKWD |
| calTw1.1J | 10 | GRCIHNGCWC ERSAPHGNCC NTSGCTATFW CPGTKFD |
| calTw1.1K | 11 | GRCIENGCWC ERSAPHGNCC NTSGCTARWW CPGTKFD |
| calTw1.1L | 12 | GRCIENGCWC ERSAPHGNCC NTSGCTARWW CPGTKWD |
| calTw1.1M | 13 | GRCIHNGCFC EESKPNGNCC DTGGCVWWWC PGTKWD |
| calTw1.1N | 14 | GRCIHNGCFC EESKPNGNCC DTGGCVWWWC PGTKWD |
| calTw1.1O | 15 | GRCIHNGCFC EESKPNGNCC DTDGCTAAWW CPGTKWD |

TABLE 1-continued

| | | |
|---|---|---|
| calTw1.1P | 16 | GKCIHNGCFC EQDKPNGNCC DSGGCTVKWW CPGTKGD |
| calTw1.1Q | 17 | GRCIHNGCWC DEEAPHGNCC DTAGCTAWWW CPGTKFD |
| calTw1.1R | 18 | GRCIHNGCWC ERSAPHGNCC NTSGCTATFW CPGTLFD |
| calTw1.1S | 19 | GRCIHNGCWC ERSAPHGNCC NTSGCTATFW CPGTIFD |
| calTw1.1T | 20 | GRCIHNGCWC ERSAPHGNCC NTGGCV WWW CPGTKWD |
| calTw1.1U | 21 | GRCIHNGCFC ERDAPNGNCC DTDGCTARWW CPGTKWD |
| calTw1.2 | 22 | SCVHNGCICQ NAPCCHPSGC NWANVCPGFL WDKN |
| wp57 | 23 | SCIHNGCICQ NAPCCHPSGC NWVNVCPGFL WDKN |
| Q147 | 24 | SCIHNGCICQ NAPCCHPSGC NWANVCPGFL WDKN |
| Q60 | 25 | SCIHNGCMCQ NAPCCHPSGC NWANVCPGFL WDKN |
| Q63 | 26 | SCIHNGCICQ NAPCCHPSGC NWANVCPGYL WDKN |
| Q68 | 27 | SCIHNGCICQ NAPCCHASGC NWANVCPGFL WDKN |
| Q74 | 28 | SCIHNGCICH NAPCCHPSGC NWANVCPGFL WDKN |
| | 29 | SCIHNGCICQ NAPCCHPSGC NWANVCPGFL WDKN |
| calTw2.3 | 30 | AWATRDMTNM RRGLNRPSKR CLAGSARCEF HKPSSCCSGH CIFWWCA |
| Q32 | 31 | AWATRDMTNM RRGLNRPSKR CLAGSARCEF HKPSTCCSGH CIIWWCA |
| Q40 | 32 | AWATREMTNM RRGLNRPSKR CLAGSAPCEF HKRSSCCSGH CIFWWCA |
| Q35 | 33 | AWATRDMTNM RRGLSRPSKR CIAGGQPCEF HRGYMCCSEH CIFFVCA |
| Q33 | 34 | AWATRDMTNM RRGLSRPSKR CIGGGDPCEF HRGYTCCSEH CIIWVCA |
| Q39 | 35 | AWATRDMTNM RRGLNRPSKR CIGGGDPCEF HRPYTCCSGY CIVFVCA |
| Q40 | 36 | AWATRDMTNM RRGLTRPSKR CLAGSAPCEF HRGYTCCSGH CLIWVCA |
| | 37 | AAWWCPGTKW D |
| | 38 | VCPGFLWDK N |
| | 39 | GFLWDKN |
| | 40 | PGFLWDKN |
| | 41 | GYLWDKN |
| | 42 | GFLWDKN |
| | 43 | GFLWDKN |
| | 44 | GFLWDKN |
| | 45 | GFLWDKN |
| | 46 | ARCEFHKPSS CCSGHCIFWW CA |
| | 47 | CEFHKPSTCC CIC |
| | 48 | CEFHKRSSCC |
| | 49 | CEFHRGYMCC ECFVC |
| | 50 | CEFHRGYTCC ECIVC |
| | 51 | CEFHRPYTCC YCVFVC |
| | 52 | CEFHRGYTCC CLIVC |
| | 53 | |
| | 54 | |
| | 55 | |

TABLE 1-continued

|       | | |
|---|---|---|
|          | 56 | |
| wp9;     | 57 | VARQNEGPGR DPAPCCQHPI ETCCRR |
| cl 15    | 58 | VARHNDGPGR CCCC |
| Q76      | 59 | VARTNEGPGR CCCC |
| Q81      | 60 | VARTNEGPGR CCCC |
| wp1;     | 61 | SSNKCSPGFP G |
| Q111     | 62 | SSNKCSPGFP G |
| Q114     | 63 | SSNKCSPGFP G |
| Q115     | 64 | |
| wp 23    | 65 | ETCRGGECSD EFNSDVGR |
| Q138     | 66 | ETCRGGECSD EM |
| Q141     | 67 | ETCRGGECSD EGM |
| Q137     | 68 | ETCRGGECSD EGM |
| Q144     | 69 | ETCRGGECSD EGM |
| Q136     | 70 | ETCRGGECSD EGM |
| Q142     | 71 | ETCRGCECSD EGL |
| cl 37    | 72 | QRSQCCAVKK NCCHVG |
| calTx 3.1| 73 | TIMYKTGACR TNRCR |
| wp 10    | 74 | |
|          | 75 | AEDQQEQHFD SERSGLDFVL ASHLIEGHLS SKKDFQTYFK |
| cl 163   |    | YYSENDFAGE NNCCFVKWLD DKNVFVYVFK DGLESEKY |
| calTx 2.1| 76 | QCCEEFWCIG YRCW |
| calTx 2.2| 77 | PR |
| calTx 2.4| 78 | LHESCT |
| CalTx 2.3| 79 | AWATRDMTNM RRGLNRPSKR CLAGSARCEF HKPSSCCSGH CIFWWCA |
| wp66     | 80 | YYCSSCNYEE AREEGHYVSS HLLERQGR |
| Q128     | 81 | |
| Q163     | 82 | |
| Q127     | 83 | |
| cl 81    | 84 | EQLTYGGCEG NGNRFATLED CDNACARY |
| WP54     | 85 | LDSYSYTCQS PTSSTANCEG NECVSEADW |
| Q95      | 86 | LDSYSYTQS |
| Q85      | 87 | LDSYSYTCQS CC |
| Q86      | 88 | LDSYSYTCQS YCC |
| Q90      | 89 | LDSYSYTCQS CCR |
| Q89      | 90 | PLDSYSYTCQ SSCKNVC |
|          | 91 | PHRSLQVALQ VSKGCGQYLE VIVCDSLVGV GCRFSLVARY |
| cal Tx 7 | | |
| calTx 1.1| 92 | GHCIHNGCWC DQEAPHGNCC DTDGCTAAWW CPGTKWD |

TABLE 1-continued

| | |
|---|---|
| calTx 1.2 | 93 VCICQNCCHP SCNWNVCFL |
| wp31 | 94 CSQEEVRECH DDCSGNPVRD ACQCAYDPAG SPACDCYCV EPWRR |
| Q18 | 95 CSEEELQACC HCLCQCEFC |
| Q21 | 96 CSEEELQACC HCLCQCEFC |
| Q23 | 97 VRECDDCCCC C |
| Q24 | 98 CSQEEVRECQ DCASCLCCER C |
| cal Tx9C | 99 ERSITVSRCD DNNQKQDDVI LTYCGLEQTT GCNTNPYTAA |
| cl 46-3 | 100 ERSITVSRCD DCCCSYHCNC |

What is claimed is:

1. A purified *Conus californicus* toxin having at least 90% sequence identity to the sequence set forth in SEQ ID NO:1.

2. The *Conus californicus* toxin according to claim 1, wherein said toxin comprises at least 30 contiguous amino acids of a polypeptide set forth in SEQ ID NO:1.

3. The *Conus californicus* toxin according to claim 1, wherein said toxin comprises CalTx1.1A conotoxin as set forth in SEQ ID NO:1.

4. The *Conus californicus* toxin according to claim 1, wherein said conotoxin is a mature conotoxin.

5. A composition comprising a *Conus californicus* toxin according to claim 1, wherein said composition further comprises a pharmaceutically acceptable carrier.

* * * * *

SEQUENCE LISTING

<160> NUMBER OF SEQ ID NOS: 102

<210> SEQ ID NO 1
<211> LENGTH: 87
<212> TYPE: PRT
<213> ORGANISM: CONUS CALIFORNICUS

<400> SEQUENCE: 1

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Gly Gly His Cys Ile His Asn Gly Cys Trp Cys Asp Gln Glu Ala
    50                  55                  60

Pro His Gly Asn Cys Cys Asp Thr Asp Gly Cys Thr Ala Ala Trp Trp
65                  70                  75                  80

Cys Pro Gly Thr Lys Trp Asp
                85

<210> SEQ ID NO 2
<211> LENGTH: 87
<212> TYPE: PRT
<213> ORGANISM: CONUS CALIFORNICUS

<400> SEQUENCE: 2

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Gly Gly His Cys Ile His Asn Gly Cys Trp Cys Asp Gln Asp Ala
    50                  55                  60

Pro His Gly Asn Cys Cys Asp Thr Asp Gly Cys Thr Ala Ala Trp Trp
65                  70                  75                  80

Cys Pro Gly Thr Lys Trp Asp
                85

<210> SEQ ID NO 3
<211> LENGTH: 87
<212> TYPE: PRT
<213> ORGANISM: CONUS CALIFORNICUS

<400> SEQUENCE: 3

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Gly Gly His Cys Ile His Asn Gly Cys Trp Cys Asp Gln Glu Ala
    50                  55                  60

Pro His Gly Asn Cys Cys Asn Thr Ser Gly Cys Thr Ala Arg Trp Trp
65                  70                  75                  80

Cys Pro Gly Thr Lys Phe Asp
                85

<210> SEQ ID NO 4
<211> LENGTH: 87
<212> TYPE: PRT
<213> ORGANISM: CONUS CALIFORNICUS

<400> SEQUENCE: 4

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Glu Gly Arg Cys Ile His Asn Gly Cys Trp Cys Asp Glu Glu Ala
    50                  55                  60

Pro His Gly Asn Cys Cys Asp Thr Ala Gly Cys Thr Ala Trp Trp Trp
65                  70                  75                  80

Cys Pro Gly Thr Lys Trp Asp
                85

<210> SEQ ID NO 5
<211> LENGTH: 87
<212> TYPE: PRT
<213> ORGANISM: CONUS CALIFORNICUS

<400> SEQUENCE: 5

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Glu Gly Arg Cys Ile His Asn Gly Cys Met Cys Asp Glu Tyr Ser
    50                  55                  60

Pro His Gly Asn Cys Cys Asp Thr Ala Gly Cys Thr Ala Trp Trp Trp
65                  70                  75                  80

Cys Pro Gly Thr Lys Trp Asp
                85

<210> SEQ ID NO 6
<211> LENGTH: 87
<212> TYPE: PRT
<213> ORGANISM: CONUS CALIFORNICUS

<400> SEQUENCE: 6

Met Lys Leu Thr Cys Val Leu Val Val Leu Leu Leu Leu Pro Tyr
1               5                   10                  15
Gly Asp Leu Ile Thr Asn Asn Tyr Ile Arg Gly Ala Ala Arg Lys Val
            20                  25                  30
Thr Pro Trp Arg Arg Asn Leu Lys Thr Arg Asp Val Cys Asp Ser Leu
        35                  40                  45
Val Asp Gly Arg Cys Ile His Asn Gly Cys Tyr Cys Glu Arg Asp Ala
    50                  55                  60
Pro Asn Gly Asn Cys Cys Asn Thr Asp Gly Cys Thr Ala Arg Trp Trp
65                  70                  75                  80
Cys Pro Gly Thr Lys Trp Asp
                85

<210> SEQ ID NO 7
<211> LENGTH: 87
<212> TYPE: PRT
<213> ORGANISM: CONUS CALIFORNICUS

<400> SEQUENCE: 7

Met Lys Leu Thr Cys Val Leu Val Val Leu Leu Leu Leu Pro Tyr
1               5                   10                  15
Gly Asp Leu Ile Thr Asn Asn Tyr Ile Arg Gly Ala Ala Arg Lys Val
            20                  25                  30
Thr Pro Trp Arg Arg Asn Leu Lys Thr Arg Asp Val Cys Asp Ser Leu
        35                  40                  45
Val Asp Gly Arg Cys Ile His Asn Gly Cys Tyr Cys Glu Arg Asp Ala
    50                  55                  60
Pro Glu Asn Cys Cys Asn Thr Asp Gly Cys Thr Ala Arg Trp Trp
65                  70                  75                  80
Cys Pro Gly Thr Lys Trp Asp
                85

<210> SEQ ID NO 8
<211> LENGTH: 86
<212> TYPE: PRT
<213> ORGANISM: CONUS CALIFORNICUS

<400> SEQUENCE: 8

Met Lys Leu Thr Cys Val Leu Val Val Leu Leu Leu Leu Pro Tyr
1               5                   10                  15
Gly Asp Leu Ile Thr Asn Asn Tyr Ile Arg Gly Ala Ala Arg Lys Val
            20                  25                  30
Thr Pro Trp Arg Arg Asn Leu Lys Thr Arg Asp Val Cys Glu Ser Val
        35                  40                  45
Ala Gly Arg Cys Ile His Asn Gly Cys Trp Cys Glu Arg Ser Ala Pro
    50                  55                  60
His Gly Asn Cys Cys Asn Thr Ser Gly Cys Thr Ala Arg Trp Trp Cys
65                  70                  75                  80
Pro Gly Thr Lys Phe Asp
                85

<210> SEQ ID NO 9

<211> LENGTH: 87
<212> TYPE: PRT
<213> ORGANISM: CONUS CALIFORNICUS

<400> SEQUENCE: 9

Met Lys Leu Thr Cys Val Leu Val Val Leu Leu Leu Leu Pro Tyr
1               5                   10                  15
Gly Asp Leu Ile Thr Asn Asn Tyr Ile Arg Gly Ala Ala Arg Lys Val
            20                  25                  30
Thr Pro Trp Arg Arg Asn Leu Lys Thr Arg Asp Val Cys Asp Ser Leu
        35                  40                  45
Val Asp Gly Arg Cys Ile His Asn Gly Cys Phe Cys Glu Arg Ser Ala
    50                  55                  60
Pro His Gly Asn Cys Cys Asn Thr Ser Gly Cys Thr Val Arg Trp Trp
65                  70                  75                  80
Cys Pro Gly Thr Lys Trp Asp
                85

<210> SEQ ID NO 10
<211> LENGTH: 87
<212> TYPE: PRT
<213> ORGANISM: CONUS CALIFORNICUS

<400> SEQUENCE: 10

Met Lys Leu Thr Cys Val Leu Val Val Leu Leu Leu Leu Pro Tyr
1               5                   10                  15
Gly Asp Leu Ile Thr Asn Asn Tyr Ile Arg Gly Ala Ala Arg Lys Val
            20                  25                  30
Thr Pro Trp Arg Arg Asn Leu Lys Thr Arg Asp Val Cys Asp Ser Leu
        35                  40                  45
Val Gly Gly Arg Cys Ile His Asn Gly Cys Trp Cys Glu Arg Ser Ala
    50                  55                  60
Pro His Gly Asn Cys Cys Asn Thr Ser Gly Cys Thr Ala Thr Phe Trp
65                  70                  75                  80
Cys Pro Gly Thr Lys Phe Asp
                85

<210> SEQ ID NO 11
<211> LENGTH: 87
<212> TYPE: PRT
<213> ORGANISM: CONUS CALIFORNICUS

<400> SEQUENCE: 11

Met Lys Leu Thr Cys Val Leu Val Val Leu Leu Leu Leu Pro Tyr
1               5                   10                  15
Gly Asp Leu Ile Thr Asn Asn Tyr Ile Arg Gly Ala Ala Arg Lys Val
            20                  25                  30
Thr Pro Trp Arg Arg Asn Leu Lys Thr Arg Asp Val Cys Asp Ser Leu
        35                  40                  45
Val Gly Gly Arg Cys Ile His Asn Gly Cys Trp Cys Glu Arg Ser Ala
    50                  55                  60
Pro His Gly Asn Cys Cys Asn Thr Ser Gly Cys Thr Ala Arg Trp Trp
65                  70                  75                  80
Cys Pro Gly Thr Lys Phe Asp
                85

<210> SEQ ID NO 12
<211> LENGTH: 87

```
<212> TYPE: PRT
<213> ORGANISM: CONUS CALIFORNICUS

<400> SEQUENCE: 12

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
                20                  25                  30

Thr Pro Trp Arg Arg Asn Leu Lys Thr Arg Asp Val Cys Asp Ser Leu
            35                  40                  45

Val Gly Gly Arg Cys Ile His Asn Gly Cys Trp Cys Glu Arg Ser Ala
    50                  55                  60

Pro His Gly Asn Cys Cys Asn Thr Ser Gly Cys Thr Ala Arg Trp Trp
65                  70                  75                  80

Cys Pro Gly Thr Lys Trp Asp
                85

<210> SEQ ID NO 13
<211> LENGTH: 86
<212> TYPE: PRT
<213> ORGANISM: CONUS CALIFORNICUS

<400> SEQUENCE: 13

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
                20                  25                  30

Thr Pro Trp Arg Arg Asn Leu Lys Thr Arg Asp Val Cys Asp Ser Leu
            35                  40                  45

Val Asp Gly Arg Cys Ile His Asn Gly Cys Phe Cys Glu Glu Ser Lys
    50                  55                  60

Pro Asn Gly Asn Cys Cys Asp Thr Gly Gly Cys Val Trp Trp Trp Cys
65                  70                  75                  80

Pro Gly Thr Lys Trp Asp
                85

<210> SEQ ID NO 14
<211> LENGTH: 86
<212> TYPE: PRT
<213> ORGANISM: CONUS CALIFORNICUS

<400> SEQUENCE: 14

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
                20                  25                  30

Thr Pro Trp Arg Arg Asn Leu Lys Thr Arg Asp Val Cys Asp Ser Leu
            35                  40                  45

Val Asp Gly Arg Cys Ile His Asn Gly Cys Phe Cys Glu Glu Ser Lys
    50                  55                  60

Pro Asn Gly Asn Cys Cys Asp Thr Gly Gly Cys Val Trp Trp Trp Cys
65                  70                  75                  80

Pro Gly Thr Lys Trp Asp
                85

<210> SEQ ID NO 15
<211> LENGTH: 87
<212> TYPE: PRT
```

-continued

<213> ORGANISM: CONUS CALIFORNICUS

<400> SEQUENCE: 15

Met Lys Leu Thr Cys Val Leu Val Leu Leu Leu Leu Pro Tyr
1               5                   10                  15

Gly Asp Leu Ile Thr Asn Asn Tyr Ile Arg Gly Ala Ala Arg Lys Val
                20                  25                  30

Thr Pro Trp Arg Arg Asn Leu Lys Thr Arg Asp Val Cys Asp Ser Leu
            35                  40                  45

Val Gly Gly Arg Cys Ile His Asn Gly Cys Phe Cys Glu Glu Ser Lys
50                  55                  60

Pro Asn Gly Asn Cys Cys Asp Thr Asp Gly Cys Thr Ala Ala Trp Trp
65                  70                  75                  80

Cys Pro Gly Thr Lys Trp Asp
                85

<210> SEQ ID NO 16
<211> LENGTH: 86
<212> TYPE: PRT
<213> ORGANISM: CONUS CALIFORNICUS

<400> SEQUENCE: 16

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
                20                  25                  30

Thr Pro Trp Arg Arg Asn Leu Lys Thr Arg Asp Val Cys Lys Lys Ser
            35                  40                  45

Pro Gly Lys Cys Ile His Asn Gly Cys Phe Cys Glu Gln Asp Lys Pro
50                  55                  60

Asn Gly Asn Cys Cys Asp Ser Gly Gly Cys Thr Val Lys Trp Trp Cys
65                  70                  75                  80

Pro Gly Thr Lys Gly Asp
                85

<210> SEQ ID NO 17
<211> LENGTH: 87
<212> TYPE: PRT
<213> ORGANISM: CONUS CALIFORNICUS

<400> SEQUENCE: 17

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
                20                  25                  30

Thr Pro Trp Arg Arg Asn Leu Lys Thr Arg Asp Val Cys Asp Ser Leu
            35                  40                  45

Val Glu Gly Arg Cys Ile His Asn Gly Cys Trp Cys Asp Glu Glu Ala
50                  55                  60

Pro His Gly Asn Cys Cys Asp Thr Ala Gly Cys Thr Ala Trp Trp Trp
65                  70                  75                  80

Cys Pro Gly Thr Lys Phe Asp
                85

<210> SEQ ID NO 18
<211> LENGTH: 87
<212> TYPE: PRT
<213> ORGANISM: CONUS CALIFORNICUS

<400> SEQUENCE: 18

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Gly Gly Arg Cys Ile His Asn Gly Cys Trp Cys Glu Arg Ser Ala
    50                  55                  60

Pro His Gly Asn Cys Cys Asn Thr Ser Gly Cys Thr Ala Thr Phe Trp
65                  70                  75                  80

Cys Pro Gly Thr Leu Phe Asp
                85

<210> SEQ ID NO 19
<211> LENGTH: 87
<212> TYPE: PRT
<213> ORGANISM: CONUS CALIFORNICUS

<400> SEQUENCE: 19

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Gly Gly Arg Cys Ile His Asn Gly Cys Trp Cys Glu Arg Ser Ala
    50                  55                  60

Pro His Gly Asn Cys Cys Asn Thr Ser Gly Cys Thr Ala Thr Phe Trp
65                  70                  75                  80

Cys Pro Gly Thr Ile Phe Asp
                85

<210> SEQ ID NO 20
<211> LENGTH: 86
<212> TYPE: PRT
<213> ORGANISM: CONUS CALIFORNICUS

<400> SEQUENCE: 20

Met Lys Leu Thr Cys Val Leu Val Val Leu Leu Leu Leu Pro Tyr
1               5                   10                  15

Gly Asp Leu Ile Thr Asn Asn Tyr Ile Arg Gly Ala Ala Arg Lys Val
            20                  25                  30

Thr Pro Trp Arg Arg Asn Leu Lys Thr Arg Asp Val Cys Asp Ser Leu
        35                  40                  45

Val Gly Gly Arg Cys Ile His Asn Gly Cys Trp Cys Glu Arg Ser Ala
    50                  55                  60

Pro His Gly Asn Cys Cys Asn Thr Gly Gly Cys Val Trp Trp Trp Cys
65                  70                  75                  80

Pro Gly Thr Lys Trp Asp
                85

<210> SEQ ID NO 21
<211> LENGTH: 87
<212> TYPE: PRT
<213> ORGANISM: CONUS CALIFORNICUS

```
<400> SEQUENCE: 21

Met Lys Leu Thr Cys Val Leu Val Val Leu Leu Leu Leu Pro Tyr
 1               5                  10                  15

Gly Asp Leu Ile Thr Asn Asn Tyr Ile Arg Gly Ala Ala Arg Lys Val
                 20                  25                  30

Thr Pro Trp Arg Arg Asn Leu Lys Thr Arg Asp Val Cys Asp Ser Leu
             35                  40                  45

Val Asp Gly Arg Cys Ile His Asn Gly Cys Phe Cys Glu Arg Asp Ala
 50                  55                  60

Pro Asn Gly Asn Cys Cys Asp Thr Asp Gly Cys Thr Ala Arg Trp Trp
 65                  70                  75                  80

Cys Pro Gly Thr Lys Trp Asp
                 85

<210> SEQ ID NO 22
<211> LENGTH: 84
<212> TYPE: PRT
<213> ORGANISM: CONUS CALIFORNICUS

<400> SEQUENCE: 22

Met Lys Leu Thr Cys Val Leu Val Val Leu Leu Val Leu Pro Phe
 1               5                  10                  15

Gly Asp Leu Ile Thr Thr Ser Asn Thr Glu Asp Asn Lys Arg Gly Ala
                 20                  25                  30

Thr Pro Trp Gln Asn Ser Leu Lys Ala Arg Gly Val Cys Ser Thr Pro
             35                  40                  45

Glu Gly Ser Cys Val His Asn Gly Cys Ile Cys Gln Asn Ala Pro Cys
 50                  55                  60

Cys His Pro Ser Gly Cys Asn Trp Ala Asn Val Cys Pro Gly Phe Leu
 65                  70                  75                  80

Trp Asp Lys Asn

<210> SEQ ID NO 23
<211> LENGTH: 84
<212> TYPE: PRT
<213> ORGANISM: CONUS CALIFORNICUS

<400> SEQUENCE: 23

Met Lys Leu Thr Cys Val Leu Val Val Leu Leu Val Leu Pro Phe
 1               5                  10                  15

Gly Asp Leu Ile Thr Thr Ser Asn Thr Glu Asp Asn Lys Arg Gly Ala
                 20                  25                  30

Thr Pro Trp Gln Asn Ser Leu Lys Ala Arg Gly Val Cys Ser Thr Pro
             35                  40                  45

Glu Gly Ser Cys Ile His Asn Gly Cys Ile Cys Gln Asn Ala Pro Cys
 50                  55                  60

Cys His Pro Ser Gly Cys Asn Trp Val Asn Val Cys Pro Gly Phe Leu
 65                  70                  75                  80

Trp Asp Lys Asn

<210> SEQ ID NO 24
<211> LENGTH: 84
<212> TYPE: PRT
<213> ORGANISM: CONUS CALIFORNICUS

<400> SEQUENCE: 24

Met Lys Leu Thr Cys Val Leu Val Val Leu Leu Leu Val Leu Pro Phe
```

-continued

```
                1               5                  10                 15
Gly Asp Leu Ile Thr Thr Ser Asn Thr Glu Asp Asn Lys Arg Gly Ala
            20                  25                 30

Thr Pro Trp Gln Asn Ser Leu Lys Ala Arg Gly Val Cys Ser Thr Pro
            35                  40                 45

Glu Gly Ser Cys Ile His Asn Gly Cys Ile Cys Gln Asn Ala Pro Cys
            50                  55                 60

Cys His Pro Ser Gly Cys Asn Trp Ala Asn Val Cys Pro Gly Phe Leu
65                  70                  75                     80

Trp Asp Lys Asn

<210> SEQ ID NO 25
<211> LENGTH: 84
<212> TYPE: PRT
<213> ORGANISM: CONUS CALIFORNICUS

<400> SEQUENCE: 25

Met Lys Leu Thr Cys Val Leu Val Val Leu Leu Val Leu Pro Phe
1               5                   10                 15

Gly Asp Leu Ile Thr Thr Ser Asn Thr Glu Asp Asn Lys Arg Gly Ala
            20                  25                 30

Thr Pro Trp Gln Asn Ser Leu Lys Ala Arg Gly Val Cys Ser Thr Pro
            35                  40                 45

Glu Gly Ser Cys Ile His Asn Gly Cys Met Cys Gln Asn Ala Pro Cys
            50                  55                 60

Cys His Pro Ser Gly Cys Asn Trp Ala Asn Val Cys Pro Gly Phe Leu
65                  70                  75                     80

Trp Asp Lys Asn

<210> SEQ ID NO 26
<211> LENGTH: 84
<212> TYPE: PRT
<213> ORGANISM: CONUS CALIFORNICUS

<400> SEQUENCE: 26

Met Lys Leu Thr Cys Val Leu Val Val Leu Leu Val Leu Pro Phe
1               5                   10                 15

Gly Asp Leu Ile Thr Thr Ser Asn Thr Glu Asp Asn Lys Arg Gly Ala
            20                  25                 30

Thr Pro Trp Gln Asn Ser Leu Lys Ala Arg Gly Val Cys Ser Thr Pro
            35                  40                 45

Glu Gly Ser Cys Ile His Asn Gly Cys Ile Cys Gln Asn Ala Pro Cys
            50                  55                 60

Cys His Pro Ser Gly Cys Asn Trp Ala Asn Val Cys Pro Gly Tyr Leu
65                  70                  75                     80

Trp Asp Lys Asn

<210> SEQ ID NO 27
<211> LENGTH: 84
<212> TYPE: PRT
<213> ORGANISM: CONUS CALIFORNICUS

<400> SEQUENCE: 27

Met Lys Leu Thr Cys Val Leu Val Val Leu Leu Val Leu Pro Phe
1               5                   10                 15

Gly Asp Leu Ile Thr Thr Ser Asn Thr Glu Asp Asn Lys Arg Gly Ala
            20                  25                 30
```

```
Thr Pro Trp Gln Asn Ser Leu Lys Ala Arg Gly Val Cys Ser Thr Pro
        35                  40                  45

Glu Gly Ser Cys Ile His Asn Gly Cys Ile Cys Gln Asn Ala Pro Cys
    50                  55                  60

Cys His Ala Ser Gly Cys Asn Trp Ala Asn Val Cys Pro Gly Phe Leu
65                  70                  75                  80

Trp Asp Lys Asn

<210> SEQ ID NO 28
<211> LENGTH: 84
<212> TYPE: PRT
<213> ORGANISM: CONUS CALIFORNICUS

<400> SEQUENCE: 28

Met Lys Leu Thr Cys Val Leu Val Val Leu Leu Val Leu Pro Phe
1               5                   10                  15

Gly Asp Leu Ile Thr Thr Ser Asn Thr Glu Asp Asn Lys Arg Gly Ala
        20                  25                  30

Thr Pro Trp Gln Asn Ser Leu Lys Ala Arg Gly Val Cys Ser Thr Pro
        35                  40                  45

Glu Gly Ser Cys Ile His Asn Gly Cys Ile Cys His Asn Ala Pro Cys
    50                  55                  60

Cys His Pro Ser Gly Cys Asn Trp Ala Asn Val Cys Pro Gly Phe Leu
65                  70                  75                  80

Trp Asp Lys Asn

<210> SEQ ID NO 29
<211> LENGTH: 84
<212> TYPE: PRT
<213> ORGANISM: CONUS CALIFORNICUS

<400> SEQUENCE: 29

Met Lys Leu Thr Cys Val Leu Val Val Leu Leu Val Leu Pro Phe
1               5                   10                  15

Gly Asp Leu Ile Thr Thr Ser Asn Thr Glu Asp Asn Lys Arg Gly Ala
        20                  25                  30

Thr Pro Trp Gln Asn Ser Leu Lys Ala Arg Gly Val Cys Ser Thr Pro
        35                  40                  45

Glu Gly Ser Cys Ile His Asn Gly Cys Ile Cys Gln Asn Ala Pro Cys
    50                  55                  60

Cys His Pro Ser Gly Cys Asn Trp Ala Asn Val Cys Pro Gly Phe Leu
65                  70                  75                  80

Trp Asp Lys Asn

<210> SEQ ID NO 30
<211> LENGTH: 97
<212> TYPE: PRT
<213> ORGANISM: CONUS CALIFORNICUS

<400> SEQUENCE: 30

Met Lys Leu Thr Thr Val Leu Val Val Ala Leu Leu Val Leu Ala Ala
1               5                   10                  15

Cys Gln Phe Thr Val Thr Asp Asn Ser Gly Asp Pro Glu Asn Pro
        20                  25                  30

Ser Leu Arg Ser Val Gly Glu Asn Gln Asn Pro Asp Ser Thr Lys Thr
        35                  40                  45
```

```
Ile Thr Ala Trp Ala Thr Arg Asp Met Thr Asn Met Arg Arg Gly Leu
        50                  55                  60

Asn Arg Pro Ser Lys Arg Cys Leu Ala Gly Ser Ala Arg Cys Glu Phe
65                  70                  75                  80

His Lys Pro Ser Ser Cys Cys Ser Gly His Cys Ile Phe Trp Trp Cys
                85                  90                  95

Ala

<210> SEQ ID NO 31
<211> LENGTH: 97
<212> TYPE: PRT
<213> ORGANISM: CONUS CALIFORNICUS

<400> SEQUENCE: 31

Met Lys Leu Thr Thr Val Leu Val Val Ala Leu Leu Val Leu Ala Ala
1               5                   10                  15

Cys Gln Phe Thr Val Thr Asp Asn Ser Gly Asp Asp Pro Glu Asn Pro
            20                  25                  30

Ser Leu Arg Ser Val Gly Glu Asn Gln Asn Pro Asp Ser Thr Lys Thr
        35                  40                  45

Ile Thr Ala Trp Ala Thr Arg Asp Met Thr Asn Met Arg Arg Gly Leu
        50                  55                  60

Asn Arg Pro Ser Lys Arg Cys Leu Ala Gly Ser Ala Arg Cys Glu Phe
65                  70                  75                  80

His Lys Pro Ser Thr Cys Cys Ser Gly His Cys Ile Ile Trp Trp Cys
                85                  90                  95

Ala

<210> SEQ ID NO 32
<211> LENGTH: 97
<212> TYPE: PRT
<213> ORGANISM: CONUS CALIFORNICUS

<400> SEQUENCE: 32

Met Lys Leu Thr Thr Val Leu Val Val Ala Leu Leu Val Leu Ala Ala
1               5                   10                  15

Cys Gln Phe Thr Val Thr Asp Asn Ser Gly Asp Asp Pro Glu Asn Pro
            20                  25                  30

Ser Leu Arg Ser Val Gly Glu Asn Gln Asn Pro Asp Ser Thr Lys Thr
        35                  40                  45

Ile Thr Ala Trp Ala Thr Arg Asp Met Thr Asn Met Arg Arg Gly Leu
        50                  55                  60

Asn Arg Pro Ser Lys Arg Cys Leu Ala Gly Ser Ala Pro Cys Glu Phe
65                  70                  75                  80

His Lys Arg Ser Ser Cys Cys Ser Gly His Cys Ile Phe Trp Trp Cys
                85                  90                  95

Ala

<210> SEQ ID NO 33
<211> LENGTH: 97
<212> TYPE: PRT
<213> ORGANISM: CONUS CALIFORNICUS

<400> SEQUENCE: 33

Met Lys Leu Thr Thr Val Leu Val Val Ala Leu Leu Val Leu Ala Ala
1               5                   10                  15

Cys Gln Phe Thr Val Thr Asp Asn Ser Gly Asp Asp Pro Glu Asn Pro
```

```
                   20                  25                  30
Ser Leu Arg Ser Val Gly Glu Asn Gln Asn Pro Asp Ser Thr Lys Thr
            35                  40                  45

Ile Thr Ala Trp Ala Thr Arg Asp Met Thr Asn Met Arg Arg Gly Leu
     50                  55                  60

Ser Arg Pro Ser Lys Arg Cys Ile Ala Gly Gly Gln Pro Cys Glu Phe
65                   70                  75                  80

His Arg Gly Tyr Met Cys Cys Ser Glu His Cys Ile Phe Phe Val Cys
                85                  90                  95

Ala

<210> SEQ ID NO 34
<211> LENGTH: 97
<212> TYPE: PRT
<213> ORGANISM: CONUS CALIFORNICUS

<400> SEQUENCE: 34

Met Lys Leu Thr Thr Val Leu Val Val Ala Leu Leu Val Leu Ala Ala
1               5                   10                  15

Cys Gln Phe Thr Val Thr Asp Asn Ser Gly Asp Asp Pro Glu Asn Pro
            20                  25                  30

Ser Leu Arg Ser Val Gly Glu Asn Gln Asn Pro Asp Ser Thr Lys Thr
            35                  40                  45

Ile Thr Ala Trp Ala Thr Arg Asp Met Thr Asn Met Arg Arg Gly Leu
     50                  55                  60

Ser Arg Pro Ser Lys Arg Cys Ile Gly Gly Gly Asp Pro

```
Met Lys Leu Thr Thr Val Leu Val Val Ala Leu Leu Val Leu Ala Ala
 1               5                  10                  15

Cys Gln Phe Thr Val Thr Asp Asn Ser Gly Asp Asp Pro Glu Asn Pro
             20                  25                  30

Ser Leu Arg Ser Val Gly Glu Asn Gln Asn Pro Asp Ser Thr Lys Thr
             35                  40                  45

Ile Thr Ala Trp Ala Thr Arg Asp Met Thr Asn Met Arg Arg Gly Leu
 50                  55                  60

Thr Arg Pro Ser Lys Arg Cys Leu Ala Gly Ser Ala Pro Cys Glu Phe
 65                  70                  75                  80

His Arg Gly Tyr Thr Cys Cys Ser Gly His Cys Leu Ile Trp Val Cys
                 85                  90                  95

Ala
```

<210> SEQ ID NO 37
<211> LENGTH: 61
<212> TYPE: PRT
<213> ORGANISM: CONUS CALIFORNICUS

<400> SEQUENCE: 37

```
Gly Ala Ala Arg Lys Val Thr Pro Trp Arg Arg Asn Leu Lys Thr Arg
 1               5                  10                  15

Asp Val Cys Asp Ser Leu Val Gly Gly His Cys Ile His Asn Gly Cys
             20                  25                  30

Trp Cys Asp Gln Glu Ala Pro His Gly Asn Cys Cys Thr Asp Gly
             35                  40                  45

Cys Thr Ala Ala Trp Trp Cys Pro Gly Thr Lys Trp Asp
 50                  55                  60
```

<210> SEQ ID NO 38
<211> LENGTH: 58
<212> TYPE: PRT
<213> ORGANISM: CONUS CALIFORNICUS

<400> SEQUENCE: 38

```
Asp Asn Lys Arg Gly Ala Thr Pro Trp Gln Asn Ser Leu Lys Ala Arg
 1               5                  10                  15

Gly Val Cys Ser Thr Pro Glu Gly Ser Cys Val His Asn Gly Cys Ile
             20                  25                  30

Cys Gln Asn Ala Pro Cys Cys His Pro Ser Gly Cys Asn Trp Ala Asn
             35                  40                  45

Val Cys Pro Gly Phe Leu Trp Asp Lys Asn
     50                  55
```

<210> SEQ ID NO 39
<211> LENGTH: 58
<212> TYPE: PRT
<213> ORGANISM: CONUS CALIFORNICUS

<400> SEQUENCE: 39

```
Asp Asn Lys Arg Gly Ala Thr Pro Trp Gln Asn Ser Leu Lys Ala Arg
 1               5                  10                  15

Gly Val Cys Ser Thr Pro Glu Gly Ser Cys Ile His Asn Gly Cys Cys
             20                  25                  30

Gln Asn Ala Pro Gln Cys Cys His Pro Ser Gly Cys Asn Trp Ala Asn
             35                  40                  45

Val Cys Pro Gly Phe Leu Trp Asp Lys Asn
```

```
                50                  55

<210> SEQ ID NO 40
<211> LENGTH: 59
<212> TYPE: PRT
<213> ORGANISM: CONUS CALIFORNICUS

<400> SEQUENCE: 40

Asp Asn Lys Arg Gly Ala Thr Pro Trp Gln Asn Ser Leu Lys Ala Arg
 1               5                  10                  15

Gly Val Cys Ser Thr Pro Glu Gly Ser Cys Ile His Asn Gly Cys Met
                20                  25                  30

Cys Gln Asn Ala Pro Gln Cys Cys His Pro Ser Gly Cys Asn Trp Ala
            35                  40                  45

Asn Val Cys Pro Gly Phe Leu Trp Asp Lys Asn
        50                  55

<210> SEQ ID NO 41
<211> LENGTH: 58
<212> TYPE: PRT
<213> ORGANISM: CONUS CALIFORNICUS

<400> SEQUENCE: 41

Asp Asn Lys Arg Gly Ala Thr Pro Trp Gln Asn Ser Leu Lys Ala Arg
 1               5                  10                  15
Gly Val Cys Ser Thr Pro Glu Gly Ser Cys Ile His Asn Gly Cys Cys
                20                  25                  30
Gln Asn Ala Pro Gln Cys Cys His Pro Ser Gly Cys Asn Trp Ala Asn
            35                  40                  45
Val Cys Pro Gly Tyr Leu Trp Asp Lys Asn
        50                  55

<210> SEQ ID NO 42
<211> LENGTH: 58
<212> TYPE: PRT
<213> ORGANISM: CONUS CALIFORNICUS

<400> SEQUENCE: 42

Asp Asn Lys Arg Gly Ala Thr Pro Trp Gln Asn Ser Leu Lys Ala Arg
 1               5                  10                  15

Gly Val Cys Ser Thr Pro Glu Gly Ser Cys Ile His Asn Gly Cys Cys
                20                  25                  30

Gln Asn Ala Pro Gln Cys Cys His Ala Ser Gly Cys Asn Trp Ala Asn
            35                  40                  45

Val Cys Pro Gly Phe Leu Trp Asp Lys Asn
        50                  55

<210> SEQ ID NO 43
<211> LENGTH: 58
<212> TYPE: PRT
<213> ORGANISM: CONUS CALIFORNICUS

<400> SEQUENCE: 43

Asp Asn Lys Arg Gly Ala Thr Pro Trp Gln Asn Ser Leu Lys Ala Arg
 1               5                  10                  15

Gly Val Cys Ser Thr Pro Glu Gly Ser Cys Ile His Asn Gly Cys Cys
                20                  25                  30

His Asn Ala Pro Gln Cys Cys His Pro Ser Gly Cys Asn Trp Ala Asn
            35                  40                  45

Val Cys Pro Gly Phe Leu Trp Asp Lys Asn
        50                  55
```

<210> SEQ ID NO 44
<211> LENGTH: 58
<212> TYPE: PRT
<213> ORGANISM: CONUS CALIFORNICUS

<400> SEQUENCE: 44

Asp Asn Lys Arg Gly Ala Thr Pro Trp Gln Asn Ser Leu Lys Ala Arg
1               5                   10                  15

Gly Val Cys Ser Thr Pro Glu Gly Ser Cys Ile His Asn Gly Cys Cys
                20                  25                  30

Gln Asn Ala Pro Gln Cys Cys His Pro Ser Gly Cys Asn Trp Ala Asn
            35                  40                  45

Val Cys Pro Gly Phe Leu Trp Asp Lys Asn
    50                  55

<210> SEQ ID NO 45
<211> LENGTH: 58
<212> TYPE: PRT
<213> ORGANISM: CONUS CALIFORNICUS

<400> SEQUENCE: 45

Asp Asn Lys Arg Gly Ala Thr Pro Trp Gln Asn Ser Leu Lys Ala Arg
1               5                   10                  15

Gly Val Cys Ser Thr Pro Glu Gly Ser Cys Ile His Asn Gly Cys Cys
                20                  25                  30

Gln Asn Ala Pro Gln Cys Cys His Pro Ser Gly Cys Asn Trp Val Asn
            35                  40                  45

Val Cys Pro Gly Phe Leu Trp Asp Lys Asn
    50                  55

<210> SEQ ID NO 46
<211> LENGTH: 71
<212> TYPE: PRT
<213> ORGANISM: CONUS CALIFORNICUS

<400> SEQUENCE: 46

Asp Asp Pro Glu Asn Pro Ser Leu Arg Ser Val Gly Glu Asn Gln Asn
1               5                   10                  15

Pro Asp Ser Thr Lys Thr Ile Thr Ala Trp Ala Thr Arg Asp Met Thr
                20                  25                  30

Asn Met Arg Arg Gly Leu Asn Arg Pro Ser Lys Arg Cys Leu Ala Gly
            35                  40                  45

Ser Ala Arg Cys Glu Phe His Lys Pro Ser Ser Cys Cys Ser Gly His
    50                  55                  60

Cys Ile Phe Trp Trp Cys Ala
65                  70

<210> SEQ ID NO 47
<211> LENGTH: 64
<212> TYPE: PRT
<213> ORGANISM: CONUS CALIFORNICUS

<400> SEQUENCE: 47

Asp Asp Pro Glu Asn Pro Ser Leu Arg Ser Val Gly Glu Asn Gln Asn
1               5                   10                  15

Pro Asp Ser Thr Lys Thr Ile Thr Ala Trp Ala Thr Arg Asp Met Thr
                20                  25                  30

Asn Met Arg Arg Gly Leu Asn Arg Pro Ser Lys Arg Cys Leu Ala Gly
            35                  40                  45

```
Ser Ala Arg Cys Glu Phe His Lys Pro Ser Thr Cys Cys Cys Ile Cys
    50                  55                  60
```

<210> SEQ ID NO 48
<211> LENGTH: 61
<212> TYPE: PRT
<213> ORGANISM: CONUS CALIFORNICUS

<400> SEQUENCE: 48

```
Asp Asp Pro Glu Asn Pro Ser Leu Arg Ser Val Gly Glu Asn Gln Asn
 1               5                  10                  15

Pro Asp Ser Thr Lys Thr Ile Thr Ala Trp Ala Thr Arg Asp Met Thr
            20                  25                  30

Asn Met Arg Arg Gly Leu Asn Arg Pro Ser Lys Arg Cys Leu Ala Gly
        35                  40                  45

Ser Ala Pro Cys Glu Phe His Lys Arg Ser Ser Cys Cys
    50                  55                  60
```

<210> SEQ ID NO 49
<211> LENGTH: 66
<212> TYPE: PRT
<213> ORGANISM: CONUS CALIFORNICUS

<400> SEQUENCE: 49

```
Asp Asp Pro Glu Asn Pro Ser Leu Arg Ser Val Gly Glu Asn Gln Asn
 1               5                  10                  15

Pro Asp Ser Thr Lys Thr Ile Thr Ala Trp Ala Thr Arg Asp Met Thr
            20                  25                  30

Asn Met Arg Arg Gly Leu Ser Arg Pro Ser Lys Arg Cys Ile Ala Gly
        35                  40                  45

Gly Gln Pro Cys Glu Phe His Arg Gly Tyr Met Cys Cys Glu Cys Phe
    50                  55                  60

Val Cys
65
```

<210> SEQ ID NO 50
<211> LENGTH: 66
<212> TYPE: PRT
<213> ORGANISM: CONUS CALIFORNICUS

<400> SEQUENCE: 50

```
Asp Asp Pro Glu Asn Pro Ser Leu Arg Ser Val Gly Glu Asn Gln Asn
 1               5                  10                  15

Pro Asp Ser Thr Lys Thr Ile Thr Ala Trp Ala Thr Arg Asp Met Thr
            20                  25                  30

Asn Met Arg Arg Gly Leu Ser Arg Pro Ser Lys Arg Cys Ile Gly Gly
        35                  40                  45

Gly Asp Pro Cys Glu Phe His Arg Gly Tyr Thr Cys Cys Glu Cys Ile
    50                  55                  60

Val Cys
65
```

<210> SEQ ID NO 51
<211> LENGTH: 67
<212> TYPE: PRT
<213> ORGANISM: CONUS CALIFORNICUS

<400> SEQUENCE: 51

```
Asp Asp Pro Glu Asn Pro Ser Leu Arg Ser Val Gly Glu Asn Gln Asn
```

-continued

```
                 1               5                  10                 15
Pro Asp Ser Thr Lys Thr Ile Thr Ala Trp Ala Thr Arg Asp Met Thr
                    20                  25                  30

Asn Met Arg Arg Gly Leu Asn Arg Pro Ser Lys Arg Cys Ile Gly Gly
                    35                  40                  45

Gly Asp Pro Cys Glu Phe His Arg Pro Tyr Thr Cys Cys Tyr Cys Val
    50                  55                  60

Phe Val Cys
65

<210> SEQ ID NO 52
<211> LENGTH: 66
<212> TYPE: PRT
<213> ORGANISM: CONUS CALIFORNICUS

<400> SEQUENCE: 52

Asp Asp Pro Glu Asn Pro Ser Leu Arg Ser Val Gly Glu Asn Gln Asn
1               5                  10                 15

Pro Asp Ser Thr Lys Thr Ile Thr Ala Trp Ala Thr Arg Asp Met Thr
                    20                  25                  30

Asn Met Arg Arg Gly Leu Thr Arg Pro Ser Lys Arg Cys Leu Ala Gly
                    35                  40                  45

Ser Ala Pro Cys Glu Phe His Arg Gly Tyr Thr Cys Cys Cys Leu Ile
    50                  55                  60

Val Cys
65

<210> SEQ ID NO 53
<211> LENGTH: 38
<212> TYPE: PRT
<213> ORGANISM: CONUS CALIFORNICUS

<400> SEQUENCE: 53

Arg Ala Ile Ala Ser Arg Leu Arg Pro Thr Lys Arg His Cys Gly Gln
1               5                  10                 15

Asn Val Cys Leu Met Leu Ala Gly Gln Cys Cys Glu Glu Phe Trp Cys
                    20                  25                  30

Ile Gly Tyr Arg Cys Trp
        35

<210> SEQ ID NO 54
<211> LENGTH: 38
<212> TYPE: PRT
<213> ORGANISM: CONUS CALIFORNICUS
<220> FEATURE:
<221> NAME/KEY: VARIANT
<222> LOCATION: 12
<223> OTHER INFORMATION: Xaa = Any Amino Acid

<400> SEQUENCE: 54

Tyr Pro Lys Trp Leu Arg Gly Leu Ser Thr Asp Xaa Ser Glu Arg Gly
1               5                  10                 15

Cys Trp Leu Cys Leu Gly Pro Asn Ala Cys Cys Arg Gly Ser Val Cys
                    20                  25                  30

His Asn Tyr Cys Pro Arg
        35

<210> SEQ ID NO 55
<211> LENGTH: 43
<212> TYPE: PRT
```

<213> ORGANISM: CONUS CALIFORNICUS

<400> SEQUENCE: 55

Tyr Arg Lys Trp Arg Arg Ser Gly Thr Ser Thr Gly Met Arg Leu Gly
1               5                   10                  15

Ser Arg Asp Cys Gly Pro Trp Cys Trp Gly Gln Asn Lys Cys Cys Pro
            20                  25                  30

Asp Ser Cys Arg Ser Leu His Glu Ser Cys Thr
        35                  40

<210> SEQ ID NO 56
<211> LENGTH: 39
<212> TYPE: PRT
<213> ORGANISM: CONUS CALIFORNICUS

<400> SEQUENCE: 56

Asp Arg Glu Trp Arg Asp Leu Glu Trp Leu Arg Ser Leu Lys Ala His
1               5                   10                  15

Asp Lys Arg Ala Gly Cys Cys Pro Thr Ile Met Tyr Lys Thr Gly Ala
            20                  25                  30

Cys Arg Thr Asn Arg Cys Arg
        35

<210> SEQ ID NO 57
<211> LENGTH: 76
<212> TYPE: PRT
<213> ORGANISM: CONUS CALIFORNICUS

<400> SEQUENCE: 57

Met Arg Phe Tyr Ile Gly Leu Met Ala Ala Leu Met Leu Thr Ser Val
1               5                   10                  15

Leu Arg Thr Asp Ser Ala Ser Val Gly Gln Thr Gly Thr Lys Ser Glu
            20                  25                  30

Leu Ala Val Ile Glu Arg Val Ile Arg Gln Arg Asp Ala Ala Asp Val
        35                  40                  45

Lys Pro Val Ala Arg Gln Asn Glu Gly Pro Gly Arg Asp Pro Ala Pro
    50                  55                  60

Cys Cys Gln His Pro Ile Glu Thr Cys Cys Arg Arg
65                  70                  75

<210> SEQ ID NO 58
<211> LENGTH: 64
<212> TYPE: PRT
<213> ORGANISM: CONUS CALIFORNICUS

<400> SEQUENCE: 58

Met Arg Phe Tyr Ile Gly Leu Met Ala Ala Leu Met Leu Thr Ser Ile
1               5                   10                  15

Leu Arg Thr Asp Ser Ala Ser Val Gly Gln Thr Gly Thr Lys Ser Glu
            20                  25                  30

Leu Ala Leu Ile Glu Arg Val Ile Arg Gln Arg Asp Ala Ala Asp Val
        35                  40                  45

Lys Pro Val Ala Arg His Asn Asp Gly Pro Gly Arg Cys Cys Cys Cys
    50                  55                  60

<210> SEQ ID NO 59
<211> LENGTH: 64
<212> TYPE: PRT
<213> ORGANISM: CONUS CALIFORNICUS

<400> SEQUENCE: 59

Met Arg Phe Tyr Ile Gly Leu Met Ala Ala Leu Met Leu Thr Ser Val
1               5                   10                  15

Leu Arg Thr Asp Ser Ala Ser Val Gly Gln Thr Gly Thr Lys Ser Glu
            20                  25                  30

Leu Ala Val Ile Glu Arg Val Ile Arg Gln Arg Asp Ala Ala Asp Val
        35                  40                  45

Lys Pro Val Ala Arg Thr Asn Glu Gly Pro Gly Arg Cys Cys Cys Cys
    50                  55                  60

<210> SEQ ID NO 60
<211> LENGTH: 64
<212> TYPE: PRT
<213> ORGANISM: CONUS CALIFORNICUS

<400> SEQUENCE: 60

Met Arg Phe Tyr Ile Gly Leu Met Ala Ala Leu Met Leu Thr Ser Ile
1               5                   10                  15

Leu Arg Thr Asp Ser Ala Ser Val Asp Gln Thr Gly Ala Glu Gly Gly
            20                  25                  30

Leu Ala Leu Ile Glu Arg Val Ile Arg Gln Arg Asp Ala Ala Asp Val
        35                  40                  45

Lys Pro Val Ala Arg Thr Asn Glu Gly Pro Gly Arg Cys Cys Cys Cys
    50                  55                  60

<210> SEQ ID NO 61
<211> LENGTH: 61
<212> TYPE: PRT
<213> ORGANISM: CONUS CALIFORNICUS

<400> SEQUENCE: 61

Met Lys Phe Leu Leu Phe Leu Ser Val Ala Leu Leu Leu Thr Ser Phe
1               5                   10                  15

Ile Glu Thr Glu Ala Gly Pro Val Asn Glu Ala Gly Val Glu Arg Leu
            20                  25                  30

Phe Arg Ala Leu Val Gly Arg Gly Cys Pro Ala Asp Cys Pro Asn Thr
        35                  40                  45

Cys Asp Ser Ser Asn Lys Cys Ser Pro Gly Phe Pro Gly
    50                  55                  60

<210> SEQ ID NO 62
<211> LENGTH: 61
<212> TYPE: PRT
<213> ORGANISM: CONUS CALIFORNICUS

<400> SEQUENCE: 62

Met Lys Phe Leu Leu Phe Leu Ser Val Ala Leu Leu Leu Thr Ser Phe
1               5                   10                  15

Ile Glu Thr Glu Ala Gly Pro Val Asn Glu Ala Arg Val Glu Arg Leu
            20                  25                  30

Phe Arg Ala Leu Val Gly Arg Gly Cys Pro Ala Asp Cys Pro Asn Thr
        35                  40                  45

Cys Asp Ser Ser Asn Lys Cys Ser Pro Gly Phe Pro Gly
    50                  55                  60

<210> SEQ ID NO 63
<211> LENGTH: 61
<212> TYPE: PRT
<213> ORGANISM: CONUS CALIFORNICUS

<400> SEQUENCE: 63

Met Lys Phe Leu Leu Phe Leu Ser Val Ala Leu Leu Leu Thr Leu Phe
1               5                   10                  15

Ile Glu Thr Glu Ala Gly Pro Val Asn Glu Ala Gly Val Glu Arg Leu
            20                  25                  30

Phe Arg Ala Leu Val Gly Arg Gly Cys Pro Ala Asp Cys Pro Asn Thr
        35                  40                  45

Cys Asp Ser Ser Asn Lys Cys Ser Pro Gly Phe Pro Gly
    50                  55                  60

<210> SEQ ID NO 64
<211> LENGTH: 38
<212> TYPE: PRT
<213> ORGANISM: CONUS CALIFORNICUS

<400> SEQUENCE: 64

Met Lys Phe Leu Leu Phe Leu Ser Val Ala Leu Leu Leu Thr Ser Phe
1               5                   10                  15

Ile Glu Thr Glu Ala Gly Pro Val Asn Glu Ala Gly Val Glu Arg Leu
            20                  25                  30

Phe Arg Ala Leu Val Gly
        35

<210> SEQ ID NO 65
<211> LENGTH: 68
<212> TYPE: PRT
<213> ORGANISM: CONUS CALIFORNICUS

<400> SEQUENCE: 65

Met Lys Leu Cys Val Val Ile Val Leu Leu Met Leu Ala Met Pro Phe
1               5                   10                  15

Asn Gly Gly Glu Ala Ser Arg Phe Phe Asn Gln His Ala Arg Ser Gln
            20                  25                  30

Arg Ser Gly Met Lys Thr Arg Gly Ile Trp Cys Asp Pro Pro Cys Pro
        35                  40                  45

Lys Gly Glu Thr Cys Arg Gly Gly Glu Cys Ser Asp Glu Phe Asn Ser
    50                  55                  60

Asp Val Gly Arg
65

<210> SEQ ID NO 66
<211> LENGTH: 62
<212> TYPE: PRT
<213> ORGANISM: CONUS CALIFORNICUS

<400> SEQUENCE: 66

Met Lys Leu Cys Val Val Ile Val Leu Leu Met Leu Ala Met Pro Phe
1               5                   10                  15

Asn Gly Gly Glu Ala Ser Arg Phe Phe Asn Gln His Ala Arg Ser Gln
            20                  25                  30

Arg Ser Gly Met Lys Thr Arg Gly Ile Trp Cys Asp Pro Pro Cys Pro
        35                  40                  45

Glu Gly Glu Thr Cys Arg Gly Gly Glu Cys Ser Asp Glu Met
    50                  55                  60

<210> SEQ ID NO 67
<211> LENGTH: 63
<212> TYPE: PRT

<213> ORGANISM: CONUS CALIFORNICUS

<400> SEQUENCE: 67

Met Lys Leu Cys Val Val Ile Val Leu Leu Met Leu Ala Met Pro Phe
1               5                   10                  15

Asn Gly Gly Glu Ala Ser Arg Phe Phe Asn Gln His Ala Arg Ser Gln
            20                  25                  30

Arg Ser Gly Met Lys Thr Arg Gly Ile Trp Cys Asp Pro Pro Cys Pro
        35                  40                  45

Glu Gly Glu Thr Cys Arg Gly Gly Glu Cys Ser Asp Glu Gly Met
    50                  55                  60

<210> SEQ ID NO 68
<211> LENGTH: 63
<212> TYPE: PRT
<213> ORGANISM: CONUS CALIFORNICUS

<400> SEQUENCE: 68

Met Lys Leu Cys Val Val Leu Val Leu Met Leu Ala Met Pro Phe
1               5                   10                  15

Asn Gly Gly Glu Ala Ser Arg Phe Phe Asn Gln His Ala Arg Ser Gln
            20                  25                  30

Arg Ser Gly Met Lys Thr Arg Gly Ile Trp Cys Asp Pro Pro Cys Pro
        35                  40                  45

Glu Gly Glu Thr Cys Arg Gly Gly Glu Cys Ser Asp Glu Gly Met
    50                  55                  60

<210> SEQ ID NO 69
<211> LENGTH: 63
<212> TYPE: PRT
<213> ORGANISM: CONUS CALIFORNICUS

<400> SEQUENCE: 69

Met Lys Leu Cys Val Val Ile Val Leu Leu Met Leu Ala Met Pro Phe
1               5                   10                  15

Asn Gly Gly Glu Ala Ser Arg Phe Phe Asn Gln His Ala Arg Ser Gln
            20                  25                  30

Arg Ser Gly Met Lys Thr Arg Gly Ile Trp Cys Asp Pro Pro Cys Pro
        35                  40                  45

Asp Gly Glu Thr Cys Arg Gly Gly Glu Cys Ser Asp Glu Gly Met
    50                  55                  60

<210> SEQ ID NO 70
<211> LENGTH: 63
<212> TYPE: PRT
<213> ORGANISM: CONUS CALIFORNICUS

<400> SEQUENCE: 70

Met Lys Leu Cys Val Val Ile Val Leu Leu Met Leu Ala Met Pro Phe
1               5                   10                  15

Asn Gly Gly Glu Ala Ser Arg Phe Phe Asn Gln His Ala Arg Ser Gln
            20                  25                  30

Arg Ser Gly Met Lys Thr Arg Gly Ile Trp Cys Asp Pro Pro Cys Pro
        35                  40                  45

Glu Gly Glu Thr Cys Arg Gly Gly Glu Cys Ser Asp Glu Gly Met
    50                  55                  60

<210> SEQ ID NO 71
<211> LENGTH: 63

```
<212> TYPE: PRT
<213> ORGANISM: CONUS CALIFORNICUS

<400> SEQUENCE: 71

Met Lys Leu Cys Val Val Ile Val Leu Leu Met Leu Ala Met Pro Phe
 1               5                  10                  15

Asn Gly Gly Glu Ala Ser Arg Phe Phe Asn Gln His Ala Arg Ser Gln
            20                  25                  30

Arg Ser Gly Met Lys Thr Arg Gly Ile Trp Cys Asp Pro Pro Cys Pro
        35                  40                  45

Glu Gly Glu Thr Cys Arg Gly Glu Cys Ser Asp Glu Gly Leu
    50                  55                  60

<210> SEQ ID NO 72
<211> LENGTH: 66
<212> TYPE: PRT
<213> ORGANISM: CONUS CALIFORNICUS

<400> SEQUENCE: 72

Met Met Tyr Cys Leu Pro Val Val Cys Ile Leu Leu Leu Ile Pro
 1               5                  10                  15

Ser Ser Ala Thr Phe Val Val Glu Ser Arg Leu Glu Lys Asp Gln Ala
            20                  25                  30

Gln Ser Phe Thr Gly Asp Ala Trp Lys Arg Val Ser Pro Ile His Glu
        35                  40                  45

Met Ile Gln Arg Ser Gln Cys Cys Ala Val Lys Lys Asn Cys Cys His
    50                  55                  60

Val Gly
65

<210> SEQ ID NO 73
<211> LENGTH: 65
<212> TYPE: PRT
<213> ORGANISM: CONUS CALIFORNICUS

<400> SEQUENCE: 73

Met Lys Leu Thr Cys Val Phe Ile Ile Ala Val Leu Ile Leu Thr Ala
 1               5                  10                  15

Cys His Phe Ile Val Ala Asp Asp Thr Gly Asp Arg Glu Trp Arg Asp
            20                  25                  30

Leu Glu Trp Leu Arg Ser Leu Lys Ala His Asp Lys Arg Ala Gly Cys
        35                  40                  45

Cys Pro Thr Ile Met Tyr Lys Thr Gly Ala Cys Arg Thr Asn Arg Cys
    50                  55                  60

Arg
65

<210> SEQ ID NO 74
<211> LENGTH: 41
<212> TYPE: PRT
<213> ORGANISM: CONUS CALIFORNICUS

<400> SEQUENCE: 74

Met Lys Asn Glu Leu Ala Lys Ala Arg Ala Lys Ala Cys Cys Pro Ile
 1               5                  10                  15

Ile Ala Met Asp Arg Arg Gly Gly Asn Lys Leu Asp Leu Cys Cys Thr
            20                  25                  30

Phe Phe Pro Thr Phe Val Leu Phe Ser
        35                  40
```

<210> SEQ ID NO 75
<211> LENGTH: 178
<212> TYPE: PRT
<213> ORGANISM: CONUS CALIFORNICUS

<400> SEQUENCE: 75

Met Ile Ile Tyr Lys Asp Lys Met Ser Gly Glu Glu Leu Phe Thr Asp
1               5                   10                  15

Ala Phe His Val His Glu Glu Thr His Met Lys Phe Cys Gly Lys
                20                  25                  30

Leu Thr Leu Glu Lys Asp Ser Ile Asp Glu Lys Met Phe Gly Gly Asn
            35                  40                  45

Ala Ser Ala Glu Asp Gln Gln Glu Gln His Glu Asp Ser Glu Arg Ser
50                  55                  60

Gly Leu Asp Phe Val Leu Ala Ser His Leu Ile Glu Gly His Leu Ser
65                  70                  75                  80

Ser Lys Lys Asp Phe Gln Thr Tyr Phe Lys Glu Tyr Phe Lys Lys Leu
                85                  90                  95

Gln Glu Lys Lys Phe Pro Cys Pro Ala Glu Gly Glu Asp Lys Thr Glu
            100                 105                 110

Tyr Asp Cys Lys Val Lys Glu Phe Lys Lys Arg Ala Lys Gly Phe Phe
        115                 120                 125

Asp Phe Val Leu Glu Asn His Lys Asp Leu Cys Cys Tyr Tyr Ser Glu
    130                 135                 140

Asn Asp Phe Ala Gly Glu Asn Asn Cys Cys Phe Val Lys Trp Leu Asp
145                 150                 155                 160

Asp Lys Asn Val Glu Val Tyr Val Phe Lys Asp Gly Leu Glu Ser Glu
                165                 170                 175

Lys Tyr

<210> SEQ ID NO 76
<211> LENGTH: 64
<212> TYPE: PRT
<213> ORGANISM: CONUS CALIFORNICUS

<400> SEQUENCE: 76

Met Lys Leu Thr Cys Val Leu Ile Ile Ala Ala Leu Ile Leu Ser Ile
1               5                   10                  15

Ser Thr Ala Gly Gly Asp Ile Gln Lys Tyr Arg Ala Ile Ala Ser Arg
                20                  25                  30

Leu Arg Pro Thr Lys Arg His Cys Gly Gln Asn Val Cys Leu Met Leu
            35                  40                  45

Ala Gly Gln Cys Cys Glu Glu Phe Trp Cys Ile Gly Tyr Arg Cys Trp
        50                  55                  60

<210> SEQ ID NO 77
<211> LENGTH: 52
<212> TYPE: PRT
<213> ORGANISM: CONUS CALIFORNICUS
<220> FEATURE:
<221> NAME/KEY: VARIANT
<222> LOCATION: 26
<223> OTHER INFORMATION: Xaa = Any Amino Acid

<400> SEQUENCE: 77

Val Val Thr Ala Cys Gln Phe Thr Ala Ala Asp Asp Met Glu Tyr Pro
1               5                   10                  15

```
Lys Trp Leu Arg Gly Leu Ser Thr Asp Xaa Ser Glu Arg Gly Cys Trp
            20                  25                  30

Leu Cys Leu Gly Pro Asn Ala Cys Cys Arg Gly Ser Val Cys His Asn
            35                  40                  45

Tyr Cys Pro Arg
    50
```

<210> SEQ ID NO 78
<211> LENGTH: 56
<212> TYPE: PRT
<213> ORGANISM: CONUS CALIFORNICUS

<400> SEQUENCE: 78

```
Val Thr Ala Cys Gln Phe Ile Ala Ala Asp Asn Thr Glu Tyr Arg Lys
  1               5                  10                  15

Trp Arg Arg Ser Gly Thr Ser Thr Gly Met Arg Leu Gly Ser Arg Asp
            20                  25                  30

Cys Gly Pro Trp Cys Trp Gly Gln Asn Lys Cys Cys Pro Asp Ser Cys
            35                  40                  45

Arg Ser Leu His Glu Ser Cys Thr
    50                  55
```

<210> SEQ ID NO 79
<211> LENGTH: 97
<212> TYPE: PRT
<213> ORGANISM: CONUS CALIFORNICUS

<400> SEQUENCE: 79

```
Met Lys Leu Thr Thr Val Leu Val Ala Leu Leu Val Leu Ala Ala
  1               5                  10                  15

Cys Gln Phe Thr Val Thr Asp Asn Ser Gly Asp Asp Pro Glu Asn Pro
            20                  25                  30

Ser Leu Arg Ser Val Gly Glu Asn Gln Asn Pro Asp Ser Thr Lys Thr
            35                  40                  45

Ile Thr Ala Trp Ala Thr Arg Asp Met Thr Asn Met Arg Arg Gly Leu
    50                  55                  60

Asn Arg Pro Ser Lys Arg Cys Leu Ala Gly Ser Ala Arg Cys Glu Phe
 65                  70                  75                  80

His Lys Pro Ser Ser Cys Cys Ser Gly His Cys Ile Phe Trp Trp Cys
            85                  90                  95

Ala
```

<210> SEQ ID NO 80
<211> LENGTH: 78
<212> TYPE: PRT
<213> ORGANISM: CONUS CALIFORNICUS

<400> SEQUENCE: 80

```
Met Arg Phe Leu His Phe Leu Ile Val Ala Val Leu Leu Ala Ser Phe
  1               5                  10                  15

Met Glu Ser Gly Ala Met Pro Arg Asn Pro Lys Lys Lys Arg Gly Trp
            20                  25                  30

Asp Thr Pro Ala Pro Cys Arg Tyr Cys Gln Trp Asn Gly Pro Gln Cys
            35                  40                  45

Cys Val Tyr Tyr Cys Ser Ser Cys Asn Tyr Glu Glu Ala Arg Glu Glu
    50                  55                  60

Gly His Tyr Val Ser Ser His Leu Leu Glu Arg Gln Gly Arg
 65                  70                  75
```

<210> SEQ ID NO 81
<211> LENGTH: 36
<212> TYPE: PRT
<213> ORGANISM: CONUS CALIFORNICUS

<400> SEQUENCE: 81

Met Arg Phe Leu His Phe Leu Ile Val Ala Val Leu Leu Ala Ser Phe
1               5                   10                  15

Met Glu Ser Gly Ala Met Pro Arg Asn Pro Lys Lys Lys Cys Cys Cys
            20                  25                  30

Cys Cys Cys Ser
        35

<210> SEQ ID NO 82
<211> LENGTH: 36
<212> TYPE: PRT
<213> ORGANISM: CONUS CALIFORNICUS

<400> SEQUENCE: 82

Met Arg Phe Leu His Phe Leu Ile Val Ala Val Leu Leu Ala Ser Phe
1               5                   10                  15

Met Glu Ser Gly Ala Met Pro Arg Asn Pro Lys Lys Lys Cys Cys Lys
            20                  25                  30

Cys Cys Cys Cys
        35

<210> SEQ ID NO 83
<211> LENGTH: 36
<212> TYPE: PRT
<213> ORGANISM: CONUS CALIFORNICUS

<400> SEQUENCE: 83

Met Arg Phe Leu His Phe Leu Ile Val Ala Val Leu Leu Ala Ser Phe
1               5                   10                  15

Met Glu Ser Gly Ala Met Pro Arg Asn Pro Lys Lys Lys Val Cys Cys
            20                  25                  30

Cys Cys Cys Cys
        35

<210> SEQ ID NO 84
<211> LENGTH: 78
<212> TYPE: PRT
<213> ORGANISM: CONUS CALIFORNICUS

<400> SEQUENCE: 84

Met Thr Phe Leu Leu Leu Leu Val Ser Val Cys Met Met Ala Thr Gly
1               5                   10                  15

Glu Glu Arg Thr Lys Arg Asp Val Cys Glu Leu Pro Phe Glu Glu Gly
            20                  25                  30

Pro Cys Phe Ala Ala Ile Arg Val Tyr Ala Tyr Asn Ala Glu Thr Gly
        35                  40                  45

Asp Cys Glu Gln Leu Thr Tyr Gly Gly Cys Gly Asn Gly Asn Arg
    50                  55                  60

Phe Ala Thr Leu Glu Asp Cys Asp Asn Ala Cys Ala Arg Tyr
65                  70                  75

<210> SEQ ID NO 85
<211> LENGTH: 79
<212> TYPE: PRT

<213> ORGANISM: CONUS CALIFORNICUS

<400> SEQUENCE: 85

Met Asn Cys Tyr Leu Ile Leu Thr Val Ala Leu Leu Leu Thr Ser Ala
1               5                   10                  15

Met Thr Gly Thr Thr Thr Ala Gly Gln Leu Asn Lys Lys Gly Val Thr
            20                  25                  30

Leu Arg Glu Asp Asp Gly Phe Pro Cys Asn Ala Gly Asn Cys Ala Cys
        35                  40                  45

Leu Pro Leu Asp Ser Tyr Ser Tyr Thr Cys Gln Ser Pro Thr Ser Ser
    50                  55                  60

Thr Ala Asn Cys Glu Gly Asn Glu Cys Val Ser Glu Ala Asp Trp
65                  70                  75

<210> SEQ ID NO 86
<211> LENGTH: 59
<212> TYPE: PRT
<213> ORGANISM: CONUS CALIFORNICUS

<400> SEQUENCE: 86

Met Asn Cys Tyr Leu Ile Leu Thr Val Ala Leu Leu Leu Thr Ser Ala
1               5                   10                  15

Met Thr Gly Thr Thr Thr Ala Gly Gln Leu Asn Lys Lys Arg Val Thr
            20                  25                  30

Leu Arg Glu Asp Asp Gly Phe Pro Cys Asn Ala Gly Asn Cys Ala Cys
        35                  40                  45

Leu Pro Leu Asp Ser Tyr Ser Tyr Thr Gln Ser
    50                  55

<210> SEQ ID NO 87
<211> LENGTH: 62
<212> TYPE: PRT
<213> ORGANISM: CONUS CALIFORNICUS

<400> SEQUENCE: 87

Met Asn Cys Tyr Leu Ile Leu Thr Val Ala Leu Leu Leu Thr Ser Ala
1               5                   10                  15

Met Thr Gly Thr Thr Thr Ala Gly Gln Leu Asn Lys Lys Gly Val Thr
            20                  25                  30

Leu Arg Glu Asp Asp Arg Phe Pro Cys Asn Ala Gly Asn Cys Ala Cys
        35                  40                  45

Leu Pro Leu Asp Ser Tyr Ser Tyr Thr Cys Gln Ser Cys Cys
    50                  55                  60

<210> SEQ ID NO 88
<211> LENGTH: 63
<212> TYPE: PRT
<213> ORGANISM: CONUS CALIFORNICUS

<400> SEQUENCE: 88

Met Asn Cys Tyr Leu Ile Leu Thr Val Ala Leu Leu Leu Thr Ser Ala
1               5                   10                  15

Met Thr Gly Thr Thr Thr Ala Gly Gln Leu Asn Lys Lys Gly Val Thr
            20                  25                  30

Leu Arg Glu Asp Asp Arg Phe Pro Cys Asn Ala Gly Asn Cys Ala Cys
        35                  40                  45

Leu Pro Leu Asp Ser Tyr Ser Tyr Thr Cys Gln Ser Tyr Cys Cys
    50                  55                  60

```
<210> SEQ ID NO 89
<211> LENGTH: 63
<212> TYPE: PRT
<213> ORGANISM: CONUS CALIFORNICUS

<400> SEQUENCE: 89

Met Asn Cys Tyr Leu Ile Leu Thr Val Ala Leu Leu Leu Thr Ser Ala
 1               5                  10                  15

Met Thr Gly Thr Thr Thr Ala Gly Gln Leu Asn Lys Lys Gly Val Thr
                20                  25                  30

Leu Arg Glu Asp Asp Arg Phe Pro Cys Asn Ala Gly Asn Cys Ala Cys
            35                  40                  45

Leu Pro Leu Asp Ser Tyr Ser Tyr Thr Cys Gln Ser Cys Cys Arg
        50                  55                  60

<210> SEQ ID NO 90
<211> LENGTH: 67
<212> TYPE: PRT
<213> ORGANISM: CONUS CALIFORNICUS

<400> SEQUENCE: 90

Met Asn Cys Tyr Leu Ile Leu Thr Val Ala Leu Leu Leu Thr Ser Ala
 1               5                  10                  15

Met Thr Gly Thr Thr Thr Ala Gly Gln Leu Asn Lys Lys Gly Val Thr
                20                  25                  30

Gln Arg Glu Asp Asp Arg Thr Phe Pro Cys Asn Ser Gly Arg Cys Ala
            35                  40                  45

Cys Gln Pro Leu Asp Ser Tyr Ser Tyr Thr Cys Gln Ser Ser Cys Lys
        50                  55                  60

Asn Val Cys
65

<210> SEQ ID NO 91
<211> LENGTH: 122
<212> TYPE: PRT
<213> ORGANISM: CONUS CALIFORNICUS

<400> SEQUENCE: 91

Met Lys Phe Asp Gly Ser Leu Phe Leu Ala Ile Leu Leu Cys Ile Thr
 1               5                  10                  15

Met Thr Thr Lys Arg Thr Ser Ala Arg Thr Cys Asp Tyr His Asp Ile
                20                  25                  30

Ile Arg Val Gln Tyr Pro Asp Gly Arg Val Leu Ser Gly Asp Tyr Cys
            35                  40                  45

Tyr Cys Pro His Arg Ser Leu Gln Val Ala Leu Gln Val Ser Lys Gly
        50                  55                  60

Cys Gly Gln Tyr Leu Glu Val Ile Val Cys Asp Ser Leu Val Gly Val
65                  70                  75                  80

Gly Cys Arg Phe Ser Leu Val Ala Arg Tyr Asp Pro Ser Asn Gly Glu
                85                  90                  95

Glu Asp Pro Gly Met Trp Cys Arg Cys Ser Thr Tyr Ser Phe Phe Gly
            100                 105                 110

Asn Ser Arg Arg Trp Glu Asn Ser Met Trp
        115                 120

<210> SEQ ID NO 92
<211> LENGTH: 87
<212> TYPE: PRT
```

<213> ORGANISM: CONUS CALIFORNICUS

<400> SEQUENCE: 92

```
Met Lys Leu Thr Cys Val Leu Val Leu Leu Leu Leu Pro Tyr
1               5                   10                  15

Gly Asp Leu Ile Thr Asn Asn Tyr Ile Arg Gly Ala Ala Arg Lys Val
                20                  25                  30

Thr Pro Trp Arg Arg Asn Leu Lys Thr Arg Asp Val Cys Asp Ser Leu
            35                  40                  45

Val Gly Gly His Cys Ile His Asn Gly Cys Trp Cys Asp Gln Glu Ala
    50                  55                  60

Pro His Gly Asn Cys Cys Asp Thr Asp Gly Cys Thr Ala Ala Trp Trp
65                  70                  75                  80

Cys Pro Gly Thr Lys Trp Asp
                85
```

<210> SEQ ID NO 93
<211> LENGTH: 69
<212> TYPE: PRT
<213> ORGANISM: CONUS CALIFORNICUS

<400> SEQUENCE: 93

```
Met Lys Leu Thr Cys Val Leu Val Val Leu Leu Val Leu Pro Phe
1               5                   10                  15

Gly Asp Leu Ile Thr Thr Ser Asn Thr Glu Asp Asn Lys Arg Gly Ala
                20                  25                  30

Thr Pro Trp Gln Asn Ser Leu Lys Ala Arg Gly Cys Ser Thr Pro Glu
            35                  40                  45

Ser Cys Val Cys Ile Cys Gln Asn Cys Cys His Pro Ser Cys Asn Trp
    50                  55                  60

Asn Val Cys Phe Leu
65
```

<210> SEQ ID NO 94
<211> LENGTH: 94
<212> TYPE: PRT
<213> ORGANISM: CONUS CALIFORNICUS

<400> SEQUENCE: 94

```
Met Met Ser Thr Lys Gly Ile Thr Leu Phe Leu Cys Leu Leu Leu Leu
1               5                   10                  15

Ala Leu Ala Thr Ser Val Asn Gly Gly Gln Gly Thr Arg Arg Ser Arg
                20                  25                  30

Met Thr Arg Ala Leu His Gly Gly Arg Pro Ser Ala Arg Tyr Asp Ala
            35                  40                  45

Pro Tyr Cys Ser Gln Glu Glu Val Arg Glu Cys His Asp Asp Cys Ser
    50                  55                  60

Gly Asn Pro Val Arg Asp Ala Cys Gln Cys Ala Tyr Asp Pro Ala Gly
65                  70                  75                  80

Ser Pro Ala Cys Asp Cys Tyr Cys Val Glu Pro Trp Arg Arg
                85                  90
```

<210> SEQ ID NO 95
<211> LENGTH: 69
<212> TYPE: PRT
<213> ORGANISM: CONUS CALIFORNICUS

<400> SEQUENCE: 95

```
Met Met Ser Thr Lys Gly Ile Thr Leu Phe Leu Cys Leu Leu Leu Leu
 1               5                  10                  15

Ala Leu Ala Thr Ser Val Asn Gly Gly Gln Gly Thr Arg Arg Ser Arg
             20                  25                  30

Met Thr Arg Ala Leu His Gly Asp Arg Pro Ser Ala Arg Tyr Asp Ala
             35                  40                  45

Pro Tyr Cys Ser Glu Glu Leu Gln Ala Cys Cys His Cys Leu Cys
     50                  55                  60

Gln Cys Glu Phe Cys
 65
```

<210> SEQ ID NO 96
<211> LENGTH: 69
<212> TYPE: PRT
<213> ORGANISM: CONUS CALIFORNICUS

<400> SEQUENCE: 96

```
Met Met Ser Thr Lys Gly Ile Thr Leu Phe Leu Cys Leu Leu Leu Leu
 1               5                  10                  15

Ala Leu Ala Thr Ser Val Asn Gly Gly Gln Gly Thr Arg Arg Ser Arg
             20                  25                  30

Met Thr Arg Ala Leu His Gly Gly Arg Pro Ser Ala Arg Tyr Asp Ala
             35                  40                  45

Pro Tyr Cys Ser Glu Glu Leu Gln Ala Cys Cys His Cys Leu Cys
     50                  55                  60

Gln Cys Glu Phe Cys
 65
```

<210> SEQ ID NO 97
<211> LENGTH: 61
<212> TYPE: PRT
<213> ORGANISM: CONUS CALIFORNICUS

<400> SEQUENCE: 97

```
Met Met Ser Thr Lys Gly Ile Thr Leu Phe Leu Cys Leu Leu Leu Leu
 1               5                  10                  15

Ala Leu Ala Thr Ser Val Asn Gly Gly Gln Gly Thr Arg Arg Ser Arg
             20                  25                  30

Met Thr Arg Ala Leu His Gly Arg Tyr Asp Ala Pro Tyr Tyr Asp Ala
             35                  40                  45

Pro Tyr Val Arg Glu Cys Asp Asp Cys Cys Cys Cys
     50                  55                  60
```

<210> SEQ ID NO 98
<211> LENGTH: 71
<212> TYPE: PRT
<213> ORGANISM: CONUS CALIFORNICUS

<400> SEQUENCE: 98

```
Met Met Ser Thr Lys Gly Ile Thr Leu Phe Leu Cys Leu Leu Leu Leu
 1               5                  10                  15

Ala Leu Ala Thr Ser Val Asn Gly Gly Gln Gly Thr Arg Arg Ser Arg
             20                  25                  30

Met Thr Arg Ala Leu His Gly Gly Arg Pro Ser Ala Arg Tyr Asp Ala
             35                  40                  45

Pro Tyr Cys Ser Gln Glu Val Arg Glu Cys Gln Asp Cys Ala Ser
     50                  55                  60

Cys Leu Cys Cys Glu Arg Cys
```

```
65                  70

<210> SEQ ID NO 99
<211> LENGTH: 131
<212> TYPE: PRT
<213> ORGANISM: CONUS CALIFORNICUS

<400> SEQUENCE: 99

Met Lys Leu Leu Leu Thr Leu Leu Leu Gly Ser Ala Leu Met Cys Ile
1               5                   10                  15

Thr Leu Ala Asp Glu Cys Gly Leu Gly Thr His Arg Pro Val Lys Glu
            20                  25                  30

Val Ile Asp Asn Val Arg Thr Met Tyr Tyr Cys Asp Cys Arg Ala Gly
        35                  40                  45

Asp Ala Glu Arg Ser Ile Thr Val Ser Arg Cys Asp Asp Asn Asn Gln
    50                  55                  60

Lys Gln Asp Asp Val Ile Leu Thr Tyr Cys Gly Leu Glu Gln Thr Thr
65                  70                  75                  80

Gly Cys Asn Thr Asn Pro Tyr Thr Ala Ala Lys His Asp Ser Ser Gly
                85                  90                  95

Asp Lys Pro Gln Phe Tyr Cys Ser Cys Leu Asn Tyr Lys Tyr Glu Gln
            100                 105                 110

Ser His Ala Asp Ser Arg Tyr Trp Thr Ile Arg Cys Tyr Met Gly Asp
        115                 120                 125

Ile Cys Asp
    130

<210> SEQ ID NO 100
<211> LENGTH: 70
<212> TYPE: PRT
<213> ORGANISM: CONUS CALIFORNICUS

<400> SEQUENCE: 100

Met Lys Leu Leu Leu Thr Leu Leu Leu Gly Ser Ala Leu Met Cys Ile
1               5                   10                  15

Thr Leu Ala Asp Glu Cys Gly Leu Gly Thr His Arg Pro Val Lys Glu
            20                  25                  30

Val Ile Asp Asn Val Arg Thr Met Tyr Tyr Cys Asp Cys Arg Ala Gly
        35                  40                  45

Asp Ala Glu Arg Ser Ile Thr Val Ser Arg Cys Asp Asp Cys Cys Cys
    50                  55                  60

Ser Tyr His Cys Asn Cys
65                  70

<210> SEQ ID NO 101
<211> LENGTH: 32
<212> TYPE: PRT
<213> ORGANISM: CONUS CALIFORNICUS
<220> FEATURE:
<221> NAME/KEY: VARIANT
<222> LOCATION: 17, 21, 23
<223> OTHER INFORMATION: Xaa = Any Amino Acid

<400> SEQUENCE: 101

Asp Val Cys Asp Ser Leu Val Gly Gly His Cys Ile His Asn Gly Cys
1               5                   10                  15

Xaa Cys Asp Gln Xaa Ala Xaa His Gly Asn Cys Cys Asp Thr Asp Gly
            20                  25                  30
```

-continued

```
<210> SEQ ID NO 102
<211> LENGTH: 23
<212> TYPE: PRT
<213> ORGANISM: CONUS CALIFORNICUS

<400> SEQUENCE: 102

Cys Cys Pro Ile Ser Ala Gly Cys Ala Val Leu Ser Ala Pro Ser Tyr
1               5                   10                  15

Ala Met Arg Cys Val Pro Leu
            20
```